United States Patent [19]
Albrecht et al.

[11] Patent Number: 5,580,953
[45] Date of Patent: Dec. 3, 1996

[54] AMYLIN ANTAGONIST PEPTIDES AND USES THEREFOR

[75] Inventors: Elisabeth Albrecht, San Diego; Howard Jones, Poway; Laura S. L. Gaeta, La Jolla; Kathryn S. Prickett; Kevin Beaumont, both of San Diego, all of Calif.

[73] Assignee: Amylin Pharmaceuticals, Inc., San Diego, Calif.

[21] Appl. No.: 794,288

[22] Filed: Nov. 19, 1991

Related U.S. Application Data

[63] Continuation-in-part of Ser. No. 744,586, Aug. 14, 1991, abandoned.

[51] Int. Cl.$^6$ .................. A61K 38/22; C07K 14/575
[52] U.S. Cl. ............................... 530/303; 530/324
[58] Field of Search ............... 514/12; 530/303, 530/324

[56] References Cited

U.S. PATENT DOCUMENTS

| | | | |
|---|---|---|---|
| 3,941,763 | 3/1976 | Sarantakis | 350/328 |
| 5,124,314 | 6/1992 | Cooper | 514/4 |
| 5,175,146 | 12/1992 | Basava | 514/12 |
| 5,264,372 | 11/1993 | Beaumont et al. | 436/504 |
| 5,266,561 | 11/1991 | Cooper et al. | 514/12 |

OTHER PUBLICATIONS

Breimer et al. *Biochem. J.*, 255, 377–390, 1988.
Lehninger, A., *Principles of Biochemistry*, pp. 100–103.
Leighton, B., et al., *Nature*, vol. 335, No. 6191, pp. 632–635 (13 Oct. 1988).
Cooper, G. J. S., et al. *Proc. Natl. Acad. Sci USA*, vol. 85, pp. 7763–7766 (Oct. 1988).
Roberts, A. N., et al., *Proc. Natl. Acad. Sci USA*, vol. 86, pp. 9662–9666 (Dec. 1989).
Munson, P. J., et al., *Analytical Biochemistry*, 107, pp. 220–239 (1980).
Cooper, G. J. S., et al., *Biochimica et Biophysica Acta.*, 1014, pp. 247–258 (1989).

*Primary Examiner*—Michael P. Woodward
*Assistant Examiner*—Benet Prickril
*Attorney, Agent, or Firm*—Lyon & Lyon

[57] ABSTRACT

Compounds which inhibit amylin activity are provided. These compounds may be used in the treatment of conditions where it is of benefit to reduce amylin activity, including the treatment of Type 2 diabetes mellitus, impaired glucose tolerance, obesity and insulin resistance.

24 Claims, 1 Drawing Sheet

¹Lys-Cys-Asn-Thr-⁵Ala-Thr-Cys-Ala-Thr-¹⁰Gln-Arg-Leu-Ala-Asn-

¹⁵Phe-Leu-Val-His-Ser-²⁰Ser-Asn-Asn-Phe-Gly-²⁵Ala-Ile-Leu-Ser-

Ser-³⁰Thr-Asn-Val-Gly-Ser-³⁵Asn-Thr-Tyr-(NH2)

*Fig. 1*

PEPTIDE A 5               10               15
Lys-Cys-Asn-Thr-Ala-Thr-Cys-Ala-Thr-Gln-Arg-Leu-Ala-Asn-Phe 20              25               30
Leu-Val-Arg-Ser-Ser-Asn-Asn-Leu-Gly-Pro-Val-Leu-Pro-Pro-Thr

35
Asn-Val-Gly-Ser-Asn-Thr-Tyr-(NH₂)

PEPTIDE B 5               10               15
Ala-Cys-Asp-Thr-Ala-Thr-Cys-Val-Thr-His-Arg-Leu-Ala-Gly-Leu 20              25               30
Leu-Ser-Arg-Ser-Gly-Gly-Val-Val-Lys-Asn-Asn-Phe-Val-Pro-Thr

35
Asn-Val-Gly-Ser-Lys-Ala-Phe-(NH₂)

PEPTIDE C 5               10               15
Cys-Ser-Asn-Leu-Ser-Thr-Cys-Val-Leu-Gly-Lys-Leu-Ser-Gln-Glu 20              25               30
Leu-His-Lys-Leu-Gln-Thr-Tyr-Pro-Arg -Thr-Asn-Thr-Gly-Ser-Gly

Thr-Pro-(NH₂)

*Fig. 2*

AMYLIN ANTAGONIST PEPTIDES AND USES THEREFOR

BACKGROUND

This application is a continuation-in-part of U.S. application Ser. No. 07/744,586, filed Aug. 14, 1991, now abandoned, for "Improved Hypoglycemics," the disclosure of which is hereby incorporated by reference.

DESCRIPTION OF THE INVENTION

This invention is directed to compounds which inhibit amylin activity. These compounds may be used in the treatment of Type 2 diabetes mellitus and other disorders, including obesity, insulin resistance, impaired glucose tolerance, disorders involving excess amylin action, and other disorders where amylin activity is benefically reduced.

DESCRIPTION OF RELATED ART AND INTRODUCTION TO THE INVENTION

The present invention is directed to compounds which inhibit amylin activity and their use as therapeutic agents for type 2 diabetes and other disorders.

Amylin is a newly discovered peptide which has marked effects on carbohydrate metabolism in vitro and in vivo including the ability to inhibit the uptake of glucose into glycogen, and the promotion of glycogenolysis in isolated skeletal muscle. Cooper, G. J. S., et al., *Proc. Natl. Acad. Sci. USA* 85: 7763–7766 (1988). A defect in amylin homeostasis is believed to contribute to insulin resistance and the development of type 2 diabetes, Cooper, G. J. S., et al., *Biochim. Biophys. Acta.* 1014: 247–258 (1989), as well as other metabolic disorders.

Amylin is 37 amino acids in length (see FIG. 1), and requires both an intact intramolecular disulfide bond and a C-terminal amide to exert its full biological activity on glycogen synthesis in skeletal muscle. E.g., Roberts, A. N., et al., *Proc. Natl. Acad. Sci. USA* 86: 9662–9666 (1989).

SUMMARY OF THE INVENTION

The present invention is directed to novel compounds which regulate the effects of amylin and amylin-like compounds (the latter compounds are also referred to as "amylin agonists"). These compounds inhibit the effects of amylin and its agonists, and are referred to as "amylin inhibitors" or amylin "antagonists."

Several assays have been developed to measure amylin activity and to evaluate new compounds. A receptor binding assay as described herein may be used to screen for or to identify compounds which bind to amylin receptors and which may, therefore, be candidate amylin agonists and antagonists. The rat soleus muscle assay may be used as a secondary procedure to screen for or to evaluate and differentiate between amylin agonists and amylin antagonists. In the soleus muscle assay, amylin and amylin agonists inhibit insulin-stimulated glycogenesis. Amylin antagonists counteract this amylin inhibition which results in the recovery of insulin-stimulated glycogenesis.

The amylin inhibitors of this invention may be subdivided into three major categories: (i) truncated peptides, (ii) structurally constrained peptides, and (iii) peptides having amino acid substitutions including the substitution of unusual or unnatural amino acids for one or more of the amino acids in the naturally occurring peptide sequence, as well as peptides having a combination of the modifications (i), (ii) and/or (iii).

Three different peptides were used in the preparation of compounds within these categories and are henceforth referred to as Peptides A, B and C. The sequences of these peptides are depicted in FIG. 2.

BRIEF DESCRIPTION OF THE DRAWINGS

FIG. 1 depicts the amino acid sequence of human amylin.

FIG. 2 depicts the amino acid sequences of Peptide A Peptide B and Peptide C.

DETAILED DESCRIPTION OF THE INVENTION

The following is a detailed description of the novel compounds of the present invention which comprise amylin inhibitors. These compounds are categorized and described according to the category of antagonist, and to the class and the peptide from which they may be prepared.

Amylin antagonists of the present invention include modified peptides of Peptide A, Peptide B and/or Peptide C (See FIG. 2).

I. TRUNCATED PEPTIDE ANTAGONISTS

Truncated peptide amylin antagonists include N-terminally deleted peptides. In order to increase amylin antagonist activity of these compounds, preferably the seven N-terminal amino acid residues (i.e., amino acids 1–7) have been deleted. More preferably, the first eight N-terminal amino acid residues have been deleted. Also included are internally deleted peptides, C-terminally deleted peptides, and peptides having a combination of deletions. These truncated peptides are based on peptides such as Peptides A, B and C, and amino acids from starting structures A, B, and C, are omitted during the synthesis of the peptide. In the case of N-terminally deleted compounds, only the residues specified are assembled. For example, $^{8-37}$Peptide A [SEQ. ID. NO. 5] contains 30 residues from the C-terminal end of Peptide A. An example of an N-terminal and C-terminal deletion peptide is $^{8-35}$Peptide B [SEQ. ID. NO. 73], which contains 28 residues and differs from Peptide B by having two fewer residues at the C-terminus and 7 fewer residues at the N-terminus. Peptides under the class "internally deleted" contain the residues specified using the numbering system used for the referenced peptide. The nomenclature includes specification of peptide sequences separated by a comma which are assembled with a peptide bond between them. For a peptide which contains an omission of residues 1 through 7 and 24 through 29 the following name would be used: $^{8-23,30-37}$Peptide. This peptide would contain 24 residues arranged in a linear fashion starting with residue 8 at the N-terminus and a peptide bond between residues 23 and 30 and ending with residue 37 at the C-terminus.

The category of antagonists of amylin comprising N-terminally deleted compounds based on Peptide A includes $^{8-37}$Peptide A [SEQ. ID. 5], and peptides which omit successive single N-terminal amino acids thereof, up to and including $^{28-37}$Peptide A [SEQ. ID. NOS. 6 to 25]. In such peptides, the $^8$Ala may be replaced with Val or other hydrophobic residues such as Leu or Nle. The $^{18}$Arg may be replaced with a His, Lys or Phe residue. The $^{19}$Ser can be replaced with residues containing a side-chain hydroxyl group including Thr. The $^{23}$Leu may be replaced with another hydrophobic residue such as Phe, 1-naphthylalanine (1-Nal), or 2-naphthylalanine (2-Nal). The $^{26}$Val may be replaced with an Ile or other hydrophobic residue such as Leu, Ala, and Nle. The $^{27}$Leu may be replaced with Tyr or Nal. The $^{29}$Pro may be replaced with Arg or Lys. The $^{35}$Asn may be replaced with Lys or Arg.

A similar series of amylin antagonists may be based on Peptide B and includes $^{8-37}$Peptide B [SEQ. ID. NO. 26] and successive single N-terminal amino acid deletions thereof, up to and including $^{28-37}$Peptide B [SEQ. ID. NOS. 27 to 46]. In such peptides, the $^{31}$Asn can be replaced with Asp, Glu, or Gln.

N-terminally truncated amylin antagonists may be derived from Peptide C [SEQ. ID. NO. 47] and include $^{8-32}$Peptide C, and successive single N-terminal amino acid deletions thereof, up to and including $^{24-32}$Peptide C [SEQ. ID. NOS. 48 to 63]. In such peptides, the $^{26}$Asn can be replaced with Ala, Asp, Gln, or Glu. Residue $^{27}$Thr may be replaced with Val. Residue $^{29}$Ser may be replaced with Ala or Gly. Residue $^{30}$Gly may be replaced with Phe, Asn, Lys, Arg or Ala. Residue $^{32}$Pro may be replaced with hydroxyproline, Thr, Tyr or Phe. These N-terminally deleted compounds based on Peptide C comprise a preferred group of amylin antagonists.

C-terminally deleted amylin antagonists based on Peptide A or N-terminally truncated Peptide A compounds include $^{8-36}$Peptide A [SEQ. ID. NO. 64], and successive single C-terminal amino acid deletions thereof, up to and including $^{8-29}$Peptide A [SEQ. ID. NOS. 65 to 71].

A series of C-terminally deleted antagonists derived from Peptide B or N-terminal deleted peptide B compounds includes from $^{8-36}$Peptide B [SEQ. ID. NO. 72] and successive single C-terminal amino acid deletions thereof including $^{8-29}$Peptide B [SEQ. ID. NOS. 73 to 79].

C-terminally truncated peptides which are antagonists and are based on Peptide C or N-terminal deleted Peptide C compounds include $^{8-31}$Peptide C [SEQ. ID. NO. 80], and peptides which have successive single C-terminal amino acid deletions thereof including $^{8-22}$Peptide C [SEQ. ID. NOS. 81 to 89].

It is preferred that fewer, rather than a greater number of, C-terminal amino acids be deleted. Thus, for example, $^{8-35}$Peptide A [SEQ. ID. NO. 65] is preferred over $^{8-29}$Peptide A [SEQ. ID. NO. 71].

Internally deleted peptide antagonists based on N-terminal deletion fragments of Peptide A include peptides which contain deletions between residues 19 and 29. This includes $^{8-18,20-37}$Peptide A [SEQ. ID. NO. 90], which contains residues 8 through 18 derived from Peptide A attached through a peptide bond to residues 20 through 37 of Peptide A. Further internal residues in the region of residues 20 through 29 may be successively removed resulting in the corresponding internally deleted peptides, including $^{8-18,30-37}$Peptide A [SEQ. ID. NO. 226], the smallest peptide in this series. Similarly, this class includes $^{8-28,30-37}$Peptide A [SEQ. ID. NO. 91] and successive removal of additional internal residues in the region of residues 28 through 19, which will give other internally deleted peptides including $^{8-19,30-37}$Peptide A [SEQ. ID. NO. 93]. Examples include $^{8-23,30-37}$Peptide A [SEQ. ID. NO. 93].

The series of antagonists which comprise internally deleted peptides based on N-terminal deletion fragments of Peptide B includes $^{8-18,20-37}$Peptide B [SEQ. ID. NO. 94], and peptides having successive N-terminal deletions in this region including $^{8-18,30-37}$Peptide B [SEQ. ID. NO. 95]. Similarly this class includes $^{8-28,30-37}$Peptide B [SEQ. ID. NO. 96] and peptides having successive internal deletions including $^{8-19,30-37}$Peptide B [SEQ. ID. NO. 97].

The antagonists of this class based on N-terminal deletion fragments of Peptide C include peptides which contain deletions between and/or including residues 19 and 24. This includes $^{8-23,25-32}$Peptide C [SEQ. ID. NO. 98], and peptides having successive internal deletions including $^{8-18,25-32}$Peptide C [SEQ. ID. NO. 99]. Also included is $^{8-18,30-32}$Peptide C [SEQ. ID. NO. 100] and peptides having successive C-terminal (internal) deletions including $^{8-18,24-32}$Peptide C [SEQ. ID. NO. 101]. Examples include $^{9-19,23-32}$Peptide C [SEQ. ID. NO. 102].

With regard to internal deletion peptide antagonists, it is preferred that fewer, rather than a greater number of, internal amino acids be deleted.

Peptide amylin antagonists with a combination of deletions include peptides with deletions between residue 8 and residue 10 for the N-terminal portion of the peptide and 30 and 37 for the C-terminal end. For instance, this would include $^{9-36}$Peptide A [SEQ. ID. NO. 103] and peptides having successive single C-terminal deletions to $^{9-29}$Peptide A [SEQ. ID. NOS. 104 to 110], $^{10-36}$Peptide A [SEQ. ID. NO. 111] and peptides having successive single C-terminal deletions to $^{10-29}$Peptide A [SEQ. ID. NOS. 112 to 118], and $^{11-36}$Peptide A [SEQ. ID. NO. 119] and peptides having successive single C-terminal deletions to $^{11-29}$Peptide A [SEQ. ID. NOS. 120 to 126].

This class of antagonists based on Peptide B includes peptides with deletions between residue 8 and residue 10 for the N-terminal portion of the molecule and 30 and 37 for the C-terminal portion of the peptide. Included are $^{9-36}$Peptide B [SEQ. ID. NO. 127] and peptides having successive single C-terminal deletions to $^{9-29}$Peptide B [SEQ. ID. NOS. 128 to 134], as well as similar peptides starting with $^{10-36}$Peptide B [SEQ. ID. NOS. 135 to 142] and $^{11-36}$Peptide B [SEQ. ID. NOS. 143 to 150].

These antagonists derived from Peptide C include peptides with deletions between residue 8 and residue 10 for the N-terminal end and 25 and 32 for the C-terminal end. Specifically, this would include $^{9-31}$Peptide C [SEQ. ID. NO. 151] and peptides having successive single C-terminal deletions to $^{9-24}$Peptide C [SEQ. ID. NOS. 152 to 158], as well as similar peptides starting with $^{10-31}$Peptide C [SEQ. ID. NOS. 159 to 166] and $^{11-31}$Peptide C [SEQ. ID. NOS. 167 to 174].

As above, it is preferred that fewer, rather than a greater number of, C-terminal amino acids be deleted.

II. STRUCTURALLY CONSTRAINED PEPTIDES

A. Helix Stabilization

This category of compounds includes peptides which are structurally constrained due to covalent or noncovalent bonds. Peptide amylin antagonists having constraints include peptides containing amino acid substitutions alone or in combination with covalent bonds which favor helix formation, for example, within the region of the peptide corresponding to residues 8-24 for Peptides A, B, and C. This class of peptides includes those based on any compound described herein above including N-terminally, C-terminally or internally deleted peptides or any structurally constrained compound in this category, as well as the compounds described hereinbelow which include unusual or unnatural amino acids.

Amino acid substitutions which can form a salt bridge and thus stabilize the helix include residues containing a carboxyl side-chain, such as Glu or Asp, at a residue position which may be designated "i" and a residue with a positively charged side-chain, such as Lys, Arg or Ornithine at the i+3 or i+4 residue position within the region of 8–24 for peptides based on Peptide A, B or C. This would include, for example, the following peptides: $^{15}$Glu$^{18}$Lys$^{8-37}$Peptide A [SEQ. ID. NO. 175]; $^{15}$Asp$^{18}$Orn$^{8-37}$Peptide A [SEQ. ID. NO. 176]; $^{15}$Glu$^{19}$Lys $^{8-37}$Peptide A [SEQ. ID. NO. 177]; $^{15}$Glu$^{18}$Lys$^{8-37}$Peptide B [SEQ. ID. NO. 174], $^{15}$Asp$^{18}$Orn$^{8-37}$Peptide B [SEQ. ID. NO. 179], $^{15}$Glu$^{19}$Lys$^{8-37}$Peptide B [SEQ. ID. NO. 180]; $^{15}$Glu$^{18}$Lys$^{8-32}$Peptide C [SEQ. ID. NO. 47]; $^{15}$Asp$^{18}$Orn$^{8-32}$Peptide C [SEQ. ID. NO. 181]; $^{15}$Glu$^{19}$Lys$^{8-32}$Peptide C [SEQ. ID. NO. 182]; as well as each of the above peptides from which amino acid 8 has been deleted [SEQ. ID. NOS. 183 to 190].

These amylin antagonists may also include amino acid substitutions which favor amphiphilic helix formation. The following substitutions may be made to the Peptide A, B or C structure, either singly or in combination: residue 8 can be Leu or Ala, residue 10 can be Gln, residue 11 can be Gln, Lys or Arg, residue 12 can be Trp, residue 13 can be Gln, residue 14 can be Lys, residue 15 can be Leu, Phe, Asn or Gln, residue 17 can be Gln, Val or His, residue 18 can be Arg, His, Lys or Phe, and residue 22 can be Leu.

Peptides of the truncated peptide category may have covalent bonds to stabilize helixes. The following residue substitution pairs are used to constrain these antagonist peptides: Asp or Glu at one position and Lys or ornithine at another position. These residues are condensed to form an amide bond. Alternatively, Cys residues are used as the residue pairs and are oxidized to form an intramolecular disulfide linkage. In particular, this class includes peptides where residues involved in a covalent crosslink would be at the i and i+4 residue positions in region 8–24 of Peptide A, B or C.

B. Topography Stabilization

The structurally constrained category of peptides also includes peptides which contain a covalent bond between the side-chains of two amino acids located within Peptide A, B or C alone or in combination with any of the modifications described in the truncated peptide category or elsewhere in this category. The constraints may be used alone or in combination to stabilize the topography of the peptide to encourage binding to the amylin receptor. For example, a particular constraint comprises residues 15 or 16 linked covalently to residues 31 or 32. The following residue substitution pairs may be used to facilitate this linkage: Asp or Glu at one position and Lys or ornithine at the other position. These residues are condensed to form an amide bond.

Alternatively, sulfhydryl-containing residues are used as the residue pairs at the above-noted residue positions and are oxidized to form an intramolecular disulfide linkage. Residues which can be used in any combination include L-Cys, D-Cys, L-penicillamine, and D-penicillamine. A residue which can be used at the N-terminal position to participate in a disulfide crosslink is β-mercaptopropionic acid. The following peptides are included in this class: [cyclo$^{15,32}$] $^{15}$Lys$^{32}$Asp$^{8-37}$Peptide B [SEQ. ID. NO. 191] and the cyclized form of $^{16,31}$Cys$^{8-37}$Peptide B [SEQ. ID. NO. 192], [cyclo$^{16-26}$]$^{16}$Lys$^{26}$Asp $^{8-32}$Peptide C [SEQ. ID. NO. 193] and the cyclized forms of $^{15,27}$Cys$^{8-32}$Peptide C [SEQ. ID. NO. 194].

III. UNUSUAL OR UNNATURAL AMINO ACID SUBSTITUTIONS

Peptides as described above and herein may be prepared or modified to have unusual amino acid residues such that the resultant peptide has increased binding affinity and/or increased resistance to enzymatic degradation, and thus provide amylin antagonists which possess higher activity and longer duration of activity.

For example, Lys and/or Arg residues in the peptides may be substituted with (D)-Lys and or (D)-Arg or another basic amino acid or nonbasic residue to confer greater plasma stability. Biologically active analogues of the above described peptide sequences are also included within the scope of this invention in which the stereochemistry of individual amino acids may be inverted from (L)/S to (D)/R at one or more specific sites.

Also included within this category are analogues modified by glycosylations of Asn, Ser and/or Thr residues, or sterically constrained amino acids such as C-α-methyl-amino acids and N-α-methyl amino acids.

Antagonist analogues of amylin are included within the scope of this invention which contain less peptide character. Such peptide mimetics may include, for example, one or more of the following substitutions for —CO—NH— amide bonds: depsipeptides (—CO—O—), iminomethylenes (—CH$_2$—NH—), trans-alkenes (—CH=CH—), β-enaminonitriles (—C(=CH—CN)—NH—), thioamides (—CS—NH—), thiomethylenes (—S—CH$_2$— or —CH$_2$—S—), dimethylenes (—CH$_2$—CH$_2$—), ketomethylenes (COCH$_2$), N-methyl peptides (CON(CH$_3$)) and retro-amides (—NH—CO—). Also included within this category are analogues modified by the insertion of a natural or unnatural amino acid into the peptide sequence. For instance, peptides are included which contain amino acid alkyl chains such as aminocaproicacid (Aca) within the sequence.

Biologically active amylin antagonists based on the above peptides are included which favorably increase the hydrophobicity and/or the conformation of the starting compounds. The following unusual or unnatural amino acid substitutions, singly or in combination, may be used: β-alanine, 3,4-dehydroproline, homoproline, hydroxyproline, L-3-(2'-naphthyl)-alanine, D-3-(2'-naphthyl)-alanine, cyclohexylalanine, 1-aminocyclopentanecarboxlic acid, sarcosine, β-thienyl-L-alanine, β-thienyl-D-alanine, D-3-(3-pyridyl)-alanine, aminoctanoic acid, aminocaproic acid, 7-aminoheptanoic acid, aminovaleric acid, S-acetamidomethyl-D-cysteine, S-acetamidomethyl-L-cysteine, t-butyl-D-cysteine, t-butyl-L-cysteine, S-ethyl-D-cysteine, S-ethyl-L-cysteine, L-aspartic acid(beta-benzyl ester), D-aspartic acid(beta-benzyl ester), L-glutamic acid(gamma-benzyl ester), D-glutamic acid(gamma-benzyl ester), N-epsilon-2(2-chloro-CBZ)-L-lysine, N-epsilon-(2-chloro-CBZ)-D-lysine, N-epsilon-(CBZ)-L-lysine, N-epsilon-(CBZ)-D-lysine, p-chloro-D-phenylalanine, p-nitro-L-phenylalanine, L-serine (OBzl), D-serine(OBzl), D-threonine(OBzl), L-threonine(OBzl), O-(2,6-dichlorobenzyl)-L-tyrosine, O-t-butyl-L-tyrosine, and O-t-butyl-D-tyrosine.

GENERAL SUBSTITUTIONS OF THE COMPOUNDS BASED ON PEPTIDES A, B OR C

The compounds of the present invention may include the following general substitutions. Peptides of the present invention include compounds from each of the categories or classes described above, and which include the substitutions described herein in connection with other compounds, are within their category or class, either singly or in combination, as well as substitutions described in connection with other categories or classes of peptides. The nomenclature of the compounds of the present category is used to indicate both the peptide that the sequence is based on and the modifications made to any basic peptide sequence. An amino acid preceded by a superscript number indicates that the named amino acid replaces the amino acid normally present at the amino acid position of the superscript in the basic amino acid sequence. For example, "$^{26}$Asp$^{27}$Val$^{29}$Ala-Peptide C" refers to a peptide based on the sequence of Peptide C having the following substitutions: Asp replacing Asn at residue 26, Val replacing Thr at residue 27 and Ala replacing Ser at residue 29.

A. Substitutions at N-terminal or C-terminal Ends

The N-terminus of the compounds described herein may have an X group replacing one of the hydrogens of the N-terminal amino group, where X is selected from: lower ($C_1$ to $C_8$) alkyl, aryl substituted with lower ($C_1$ to $C_8$) alkyl, lower ($C_1$ to $C_8$) acyl, aryl substituted with lower ($C_1$ to $C_8$) acyl, aroyl, heteroaroyl, cycloalkyl, cycloalkyl substituted with lower ($C_1$ to $C_8$) alkyl, cycloacyl, H-Tyr, acetyl, H-L-Nal, H-D-Nal, cyclohexanepentanoic acid, cyclohexanepropionic acid (Chp), myristic acid, adamantane carboxylic acid, adamantane acetic acid, adamantylalanine, alkylcarbamoyl, arylcarbamoyl or the free alpha amine (H). Compounds of the invention wherein X is acetyl are preferred.

The C-terminal group (CO—Z) of the compounds described herein includes compounds where Z is selected from hydroxyl, amino, alkylamino, dialkylamino, arylamino, cycloalkylamino, aralkylamino, alkoxy, cycloalkoxy, aryloxy, aralkoxy or heteraryloxy. Compounds of the invention wherein Z is amino are preferred.

B. Specific Amino Acid Substitutions to the Sequence of Peptide A

The following substitutions may be made to the amino acid sequence of Peptide A (see FIG. 2).

Residue 8: Ala can be replaced by Val or Met. Residue 9: Thr can be replaced by Leu. Residue 10: Gln can be replaced by His, Gly or Thr. Residue 11: Arg can be replaced by Lys or Thr. Residue 12: Leu can be replaced by Tyr. Residue 13: Ala can be replaced by Thr or Ser. Residue 14: Asn can be replaced by Gly, Asp or Gln. Residue 15: Phe can be replaced by Leu, Glu or Asp. Residue 16: Leu can be replaced by Phe. Residue 17: Val can be replaced by Ile, Ser, Asn or His. Residue 18: Arg can be replaced by His, or Lys. Residue 19: Ser can be replaced by Thr, Phe or Leu. Residue 20: Ser can be replaced by Asn or Gly. Residue 21: Asn can be replaced by His or Gly. Residue 22: Asn can be replaced by Val or Met. Residue 23: Leu can be replaced by Phe, Val or Gly. Residue 24: Gly can be replaced by Asn or Lys. Residue 25: Pro can be replaced by Ala, Asn, Ser or Asp. Residue 26: Val can be replaced by Ala, Ile or Asn. Residue 27: Leu can be replaced by Phe. Residue 28: Pro can be replaced by Ser, Leu or Val. Residue 29: Pro can be replaced by Gln, Ser, Lys or Arg. Residue 31: Asn can be replaced by Asp, Ala or Ser. Residue 32: Val can be replaced by Thr or Ile. Residue 33: Gly can be replaced by Asn. Residue 34: Ser can be replaced by Ala or Val. Residue 35: Asn can be replaced by Lys, Arg, Glu or Gly. Residue 36: Thr can be replaced by Ala. Residue 37: Tyr can be replaced by Phe, Pro or hydroxyproline.

C. Specific Amino Acid Substitutions to the Sequence of Peptide B

The following substitutions may be made to the amino acid sequence of Peptide B (see FIG. 2).

Residue 8: Val can be replaced by Ala or Met. Residue 9: Thr can be replaced by Leu. Residue 10: His can be replaced by Gln, Gly or Thr. Residue 11: Arg can be replaced by Lys or Thr. Residue 12: Leu can be replaced by Tyr. Residue 13: Ala can be replaced by Thr or Ser. Residue 14: Gly can be replaced by Asn or Gln. Residue 15: Leu can be replaced by Phe, Glu or Asp. Residue 16: Leu can be replaced by Phe. Residue 17: Ser can be replaced by Ile, Val, Asn or His. Residue 18: Arg can be replaced by His or Lys. Residue 19: Ser can be replaced by Thr, Phe or Leu. Residue 20: Gly can be replaced by Ser or Asn. Residue 21: Gly can be replaced by Asn or His. Residue 22: Val can be replaced by Asn or Met. Residue 23: Val can be replaced by Phe, Leu or Gly. Residue 24: Lys can be replaced by Asn or Gly. Residue 25: Asn can be replaced by Ala, Pro, Ser or Asp. Residue 26: Asn can be replaced by Ala, Ile or Val. Residue 27: Phe can be replaced by Leu. Residue 28: Val can be replaced by Ser, Leu or Pro. Residue 29: Pro can be replaced by Gln, Ser or Arg. Residue 31: Asn can be replaced by Asp, Ala or Ser. Residue 32: Val can be replaced by Thr or Ile. Residue 33: Gly can be replaced by Asn. Residue 34: Ser can be replaced by Ala or Val. Residue 35: Lys can be replaced by Asn, Glu or Gly. Residue 36: Ala can be replaced by Thr. Residue 37: Phe can be replaced by Tyr, Pro or hydroxyproline.

D. Specific Amino Acid Substitutions to the Sequence of Peptide C

The following substitutions may be made to the amino acid sequence of Peptide C (see FIG. 2).

Residue 8: Val can be replaced by Ala or Met. Residue 9: Leu can be replaced by Thr. Residue 10: Gly can be replaced by His, Gln or Thr. Residue 11: Lys can be replaced by Lys, Arg or Thr. Residue 12: Leu can be replaced by Tyr. Residue 13: Ser can be replaced by Ala or Thr. Residue 14: Gln can be replaced by Asn, Gly or Asp. Residue 15: Glu can be replaced by Asp, Leu, Ala or Phe. Residue 16: Leu can be replaced by Phe. Residue 17: His can be replaced by Ile, Ser, Asn or Val. Residue 18: Lys can be replaced by His or Arg. Residue 19: Leu can be replaced by Thr, Ser or Phe. Residue 20: Gln can be replaced by His. Residue 22: Tyr can be replaced by Phe. Residue 24: Arg can be replaced by Lys, Ser, homo-Arg, Orn, Gln or Pro. Residue 26: Asn can be replaced by Asp, Asn, Ala or Ser. Residue 27: Thr can be replaced by Val or Ile. Residue 29: Ser can be replaced by Ala, or Val. Residue 30: Gly can be replaced by Lys, Arg, Glu or Asn. Residue 31: Thr can be replaced by Ala. Residue 32: Pro can be replaced by Phe, Tyr or hydroxyproline. Residues 19, 20 and 21 can be replaced with aminocaproic acid.

PREFERRED ANTAGONIST COMPOUNDS

One preferred group of compounds having amylin inhibition activity includes N-terminal deletion peptides based on the amino acid sequence of Peptide C. These compounds advantageously have N-terminal deletions of amino acids 1 to 7 or 1 to 8. We have found that deletion of these N-terminal amino acids from these peptides advantageously results in significant reduction of amylin agonist activity. Optionally, these compounds include certain amino acid substitutions at certain positions in the amino acid sequence which advantageously increase amylin inhibition potency.

These N-terminal deletion peptides include $^{8\text{-}32}$Peptide C, and successive N-terminal amino acid deletions thereof including $^{24\text{-}32}$Peptide C. These peptides may include one or more of the following amino acid substitutions. Residue $^{26}$Asn may be replaced with Ala, Asp, Gln or Glu. Residue $^{27}$Thr may be replaced with Val. Residue $^{29}$Ser may be replaced with Ala or Gly. Residue $^{30}$Gly may be replaced with Asn, Lys, Arg or Ala. Residue $^{32}$Pro may be replaced with Tyr, Phe or hydroxyproline. These N-terminal deletions optionally have an acetylated N-terminal amino acid.

One group of these compounds includes peptides based on $^{8-32}$Peptide C or $^{9-32}$Peptide C. These compounds may include the above-noted amino acid substitutions. Preferred amino acid substitutions include the substitution of Arg for Lys at residues 11 and 18; the substitution of Leu for Glu at residue 15; the substitution of Asn for Gly at residue 30; and, the substitution of Tyr or hydroxyproline for Pro at residue 32. According to one preferred aspect, these compounds are acylated (especially with an acetyl group) at the N-terminus.

A second group of these compounds include those having about 9 to 11 amino acid residues. A particularly preferred class of these amylin antagonist compounds are based on $^{22-32}$Peptide C. These compounds optionally include certain amino acid substitutions at certain positions in the amino acid sequence. These amino acid substitutions include the following: the substitution of the unnatural amino acid D- or L-naphthylalanine for Tyr at residue 22, the substitution of D- or L-Asp for Asn at residue 26; the substitution of Val for Thr at residue 27; the substitution of either Asn, Phe, Lys or Arg for Gly at residue 30; and the substitution of Tyr or hydroxyproline for Pro at residue 32. Another preferred class of amylin antagonist compounds are based on $^{24-32}$Peptide C and include any or all of the above-noted amino acid substitutions to the amino acid sequence as depicted in FIG. 2.

Other permutations and/or combinations of the above described amino acid substitutions are included within the scope of the present invention.

ANTAGONIST ACTIVITY

The activity of these amylin antagonists may be evaluated using certain biological assays described herein. The receptor binding assay can identify both candidate amylin agonists and antagonists, while the soleus muscle assay distinguishes between amylin agonists and antagonists.

Preferably, these antagonist compounds exhibit activity in the receptor binding assay on the order of less than about 1 to 5 nM, preferably less than about 1 nM and more preferably less than about 50 pM. In the soleus muscle assay these compounds preferably show $IC_{50}$ values on the order of less than about 1 to 2 micro molar.

The receptor binding assay is described in U.S. patent application Ser. No. 670,231, filed on Mar. 15, 1991, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et. al. (ALLFIT, Version 2.7 (NIH, Bethesda, Md. 20892)). Munsun, P. U. and Rodbard, D., *Anal. Biochem.* 107:220–239 (1980).

Assays of biological activity of amylin preparations in the soleus muscle are performed using previously described methods (Leighton, B. and Cooper, G. J. S. (1988) *Nature* 335: 632–635; Cooper, G. J. S., Leighton, B., Dimitriadis, G. D., Parry-Billings, M., Kowalchuk, J. M., Howland, K., Rothbard, J. B., Willis, A. C. and Reid, K. B. M. (1988) *Proc. Natl. Acad. Sci. USA* 85: 7763–7766.) In summary, amylin agonist activity is assessed by measuring the inhibition of insulin-stimulated glycogen synthesis in soleus muscle in response to an amylin agonist. Amylin antagonist activity is assessed by measuring the resumption of insulin-stimulated glycogen synthesis in the presence of 100 nM rat amylin and an amylin antagonist. Concentrations of peptide dissolved in carrier-free buffers are determined by quantitative amino acid analysis, as described therein. The ability of compounds to act as antagonists in this assay is determined by measuring $IC_{50}$ values. Standard errors are determined by fitting of sigmoidal dose response curves using a four parameter logistic equation (De Lean, A., Munson, P. J., Guardabasso, V. and Rodbard, D. (1988) *ALLFIT*, Version 2.7, National Institute of Child Health and Human Development, N.I.H. Bethesda, Md., 1 diskette).

A number of amylin antagonists have been characterized using these biological assays. The N-terminally deleted peptides $^{8-37}$Peptide A, $^{8-37}$Peptide B and $^{8-32}$Peptide C, were all found to compete with amylin in the receptor binding assay. These peptides have negligible agonist activity as measured by the soleus muscle assay and were shown to act as amylin antagonists. Similar results were obtained with the antagonist compounds $^{14}$Asp$^{15}$Phe$^{23}$Gly$^{8-37}$Peptide B [SEQ. ID. NO. 195]; $^{9-37}$Peptide B [SEQ. ID. NO. 27]; $^{11-37}$Peptide B [SEQ. ID. NO. 29]; $^{18-37}$Peptide B [SEQ. ID. NO. 36]; $^{26}$Asp$^{27}$Val$^{29}$Ala$^{8-32}$Peptide C [SEQ. ID. NO. 196]; $^{30}$Asn$^{32}$Tyr$^{8-32}$Peptide C [SEQ. ID. NO. 197]; Ac-$^{9-32}$Peptide C [SEQ. ID. NO. 48]; Ac-$^{30}$Asn$^{32}$Tyr$^{9-32}$Peptide C [SEQ. ID. NO. 198]; $^{9-23}$Peptide C$^{29-37}$Peptide A [SEQ. ID. NO. 199]; Ac-$^{9-23}$Peptide C$^{29-37}$Peptide A; Adm-$^{9-23}$Peptide C$^{29-37}$Peptide A; Ac-$^{11}$Arg$^{15}$Leu$^{18}$Arg$^{30}$Asn$^{32}$Tyr$^{9-32}$Peptide C [SEQ. ID. NO. 200]; Ac-$^{11}$Arg$^{18}$Arg$^{30}$Asn$^{32}$Tyr$^{9-32}$Peptide C [SEQ. ID. NO. 201]; Ac-$^{18}$Arg$^{30}$Asn$^{32}$Tyr$^{9-32}$Peptide C [SEQ. ID. NO. 202]. Infusions of $^{8-37}$Peptide B [SEQ. ID. NO. 26], $^{8-32}$Peptide C [SEQ. ID. NO. 47], and Ac-$^{11}$Arg $^{18}$Arg$^{30}$Asp$^{32}$Tyr$^{9-32}$Peptide C [SEQ. ID. NO. 203] into rats were each observed to reverse the insulin resistance caused by administered amylin.

Compounds of the invention which lack amylin agonist activity and compete with amylin at the amylin receptor include other peptides, such as C-terminal and internal deletions of Peptide A which yield compounds having the ability to bind specifically to the amylin receptor.

SYNTHESIS OF PEPTIDES

These compounds are prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydrylamine resin used in the peptide synthesizer were purchased from Applied Biosystems Inc. (Foster City, Calif.), unless otherwise indicated. The side-chain protected amino acids used and purchased from Applied Biosystem, Inc. included the following: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu(t-Bu), Fmoc-His(Trt), Fmoc-Asn (Trt), and Fmoc-Gln (Trt). Boc-His (BOM) was purchased from Applied Biosystems, Inc. or Bachem Inc. (Torrance, Calif.). Anisole, methylsulfide, phenol, ethanedithiol, and thioanisole were obtained from Aldrich Chemical Company (Milwaukee, Wis.). Air Products and Chemicals (Allentown, Pa.) supplied HF. Ethyl ether, acetic acid and methanol were purchased from Fisher Scientific (Pittsburgh, Pa.).

Solid phase peptide synthesis was carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins were cleaved with HF (−5° C. to 0° C., 1 hour). The peptide was extracted from the resin with alternating water and acetic acid, and the filtrates were lyophilized. The Fmoc-peptide resins were cleaved according to standard methods (*Introduction to Cleavage Techniques,* Applied Biosystems, Inc., 1990, pp. 6–12). Some peptides were also assembled using an Advanced Chem Tech Synthesizer (Model MPS 350, Louisville, Ky.). Peptides were purified by RP-HPLC (preparative and analytical) using a Waters Delta Prep 3000 system. A C4, C8 or C18 preparative column (10 μ, 2.2×25 cm; Vydac, Hesperia, Calif. ) was used to isolate peptides, and purity was determined using a C4, C8 or C18 analytical column (5 μ, 0.46×25 cm; Vydac). Solvents (A=0.1% TFA/water and B=0.1 %TFA/CH$_3$CN) were delivered to the analytical column at a flowrate of 1.0 ml/min and to the preparative column at 15 ml/min. Amino acid analyses were performed on the Waters Pico Tag system and processed using the Maxima program. The peptides were hydrolyzed by vapor-phase acid hydrolysis (115° C., 20–24 h). Hydrolysates were derivatized and analyzed by standard methods (Cohen, S. A., Meys, M., and Tarrin, T. L. (1989), *The Pico Tag Method: A Manual of Advanced Techniques for Amino Acid Analysis,* pp. 11–52, Millipore Corporation, Milford, Mass.). Fast atom bombardment analysis was carried out by M-Scan, Incorporated (West Chester, Pa.). Mass calibration was performed using cesium iodide or cesium iodide/glycerol. Plasma desorption ionization analysis using time of flight detection was carried out on an Applied Biosystems Bio-Ion 20 mass spectrometer.

The compounds of the invention may also be prepared using recombinant DNA techniques, using methods now known in the art. See, e.g., Sambrook et al., *Molecular cloning: A Laboratory Manual,* 2d Ed., Cold Spring Harbor (1989).

PREPARATION OF COMPOUNDS AND PHARMACEUTICAL COMPOSITIONS

Compounds of this invention form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds of this invention are useful in view of their pharmacological properties. In particular, compounds of this invention possess activity as anti-amylin and antidiabetic agents, as evidenced by their ability to reduce hyperglycemia in mammals.

Compositions or products of the invention may conveniently be provided in the form of solutions suitable for parenteral (including intravenous, intramuscular and subcutaneous) or nasal or oral administration. In some cases, it will be convenient to provide an amylin antagonist of the invention and another hypoglycemic agent, such as a sulfonylurea, in a single composition or solution for administration together. In other cases, it may be more advantageous to administer a sulfonylurea or other hypoglycemic agent separately from said amylin inhibitor. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology,* Technical Report No. 10, Supp. 42:2S (1988). Suitable formulations including hypoglycemic agents such as sulfonylureas are known in the art.

The products of the invention will normally be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include sodium citrate-citric acid and sodium phosphate-phosphoric acid. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an antagonist compound of the invention with or without another hypoglycemic agent which will be effective in one or multiple doses to control or reestablish blood sugar at the selected level. Therapeutically effective amounts of an amylin antagonist as described herein for the treatment of Type 2 diabetes, impaired glucose tolerance and other such conditions in which amylin activity is beneficially reduced are those that decrease blood sugar levels, preferably to below from about 140 to about 190 mg/dl (fasted and fed, respectively). Therapeutically effective amounts of an amylin antagonist for the treatment of insulin resistance are those that increase the effectiveness of insulin, preferably by about 20%, as may be determined using methods described herein and known in the art. Therapeutically effective amounts of an amylin antagonist for the treatment of obesity are those that reduce amylin action by about 25% or that increase the weight loss associated with diet. As will be recognized by those in the field, an effective amount of therapeutic agent will vary with many factors including the age and weight of the patient, the patient's physical condition, the blood sugar level or decrease in amylin action to the obtained, and other factors.

Such pharmaceutical compositions are useful in the treatment of type 2 diabetes mellitus, as well as other disorders where amylin action is beneficially reduced.

The effective daily antidiabetic dose of the compounds of this invention will typically be in the range of 0.05 to about 1000 mg/day, preferably about 1 to 500 mg/day for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus.

Generally, in treating humans having Type 2 diabetes mellitus, the compounds of this invention may be administered to patients in need of such treatment in a dosage range of about 0.1 mg to 50 mg per patient generally given several times a day, thus giving a total dose of from about 0.3 mg to 200 mg per day.

To assist in understanding the present invention, the following Examples are included which describe the results of a series of experiments. The following examples relating to this invention should not, of course, be construed in specifically limiting the invention and such variations of the invention, now known or later developed, which would be within the purview of one skilled in the art are considered to fall within the scope of the invention as described herein and hereinafter claimed.

EXAMPLES

Example 1

Preparation of $^{8-32}$Peptide C [SEQ. ID. NO. 47]

$^{8-32}$Peptide C was assembled on 4-methylbenzhydrylamine resin (0.72 g, 0.69 meq/g, 0.5 mmol) using Boc-protected amino acids including Boc-His(BOM) from Applied Biosystems, Inc. Double-coupling cycles were used throughout the synthesis. Peptide-resin (0.66 g) was removed after the 15th coupling cycle, and the synthesis was completed furnishing $^{8-32}$Peptide C-resin (1.57 g) with a free N-terminal amino group. The completed resin (1.57 g) was deprotected and cleaved with HF (16 ml) in the presence of anisole (1.6 ml) and DMS (1.6 ml). The peptide was extracted with water (400 ml) and a portion (200 ml) was filtered and adjusted to 1% $CH_3CN$ with solvent B used in purification of peptides. The filtrate was applied to a prep C8 column and purified (5% B for 10 minutes, 5–20% B over 10 minutes, 20% B over 32 minutes, 20–25% over 10 minutes). Purity of fractions was determined isocratically using a C8 analytical column (22% B for 5 minutes, 22–30% B in 40 minutes, 30% B for 2 minutes). Pure fractions were pooled furnishing white peptide (99% pure fractions, 98 mg). Analytical RP-HPLC (5–22% B in 5 minutes, 22–26% B over 40 minutes, 26% B for 2 minutes, 26–100% B in 10 minutes, 100% B for 5 minutes) of the lyophilized peptide pool indicated a purity of 99%. Amino acid analysis (6M HCl, 115°) showed the following: Ala, 2.04 (2); Arg, 0.89 (1); Asx, 1.02 (1); Glx, 3.14 (3); Gly, 3.20 (3); His, 0.82 (1); Leu, 3.94 (4); Lys, 2.22 (2); Pro 2.04 (2); Ser, 2.13 (2); Thr, 4.26 (4); Tyr, 0.95 (1); Val, 0.96 (1). FAB Mass Spectrometry: $(M+H)^+$ Calculated: 2726; $(M+H)+$ Found: 2726.

Example 2

Preparation of $^{18-32}$Peptide C [SEQ. ID. NO. 57]

$^{18-32}$Peptide C was prepared in a similar way as that described in Example 1. FAB Mass Spectrometry: $(M+H)^+$ Calculated: 1619.9; $(M+H)^+$ Found: 1619.6.

Example 3

Preparation of $^{22-32}$Peptide C [SEQ. ID. NO. 61]

$^{22-32}$Peptide C was prepared in a similar way as that described in Example 1. FAB Mass Spectrometry: $(M+H)^+$ Calculated: 1150.5; $(M+H)^+$ Found: 1150.

Example 4

Preparation of $^{8-17,25-32}$Peptide C [SEQ. ID. NO. 204]

$^{8-17,25-32}$Peptide C was prepared in a similar way as that described in Example 1. FAB Mass Spectrometry: $(M+H)^+$ Calculated: 1838; $(M+H)^+$ Found: 1838.

Example 5

Preparation of $^{26}Asp^{27}Val^{29}Ala^{8-32}$Peptide C [SEQ. ID. NO. 196]

$^{26}Asp^{27}Val^{29}Ala^{8-32}$Peptide C was prepared in a similar way as that described in Example 1. FAB Mass Spectrometry: $(M+H)^+$ Calculated: 2709; $(M+H)^+$ Found: 2709.

Example 6

Preparation of $^{26}Asp^{27}Val^{29}Ala^{22-32}$Peptide C [SEQ. ID. NO. 205]

$^{26}$Asp$^{27}$Val$^{29}$Ala$^{22-32}$Peptide C was prepared in a similar way as that described in Example 1. FAB Mass Spectrometry: (M+H)$^+$ Calculated: 1133; (M+H)$^+$ Found: 1133.

Example 7

Preparation of $^{9-32}$Peptide C [SEQ. ID. NO. 48]

$^{9-32}$Peptide C was prepared as described in Example 1. FAB Mass Spectrometry: (M+H)$^+$ Calculated: 2625.4; (M+H)$^+$ Found: 2626.1.

Example 8

Preparation of Acetyl-$^{8-32}$Peptide C [SEQ. ID. NO. 47]

Ac-$^{8-32}$Peptide C was assembled and purified as described in Example 1. The peptide was acetylated on the N-terminal while it was on the resin using the automatic peptide synthesizer with acetic anhydride and the ABI "cap" cycle (Culwell, A., Davis, D., Pierce, L. (1987), *Applied Biosystems User Bulletin*, Issue No. 20, p.6–7.) FAB Mass Spectrometry: (M+H)$^+$ Calculated: 2766.5; (M+H)$^+$ Found: 2766.8.

Example 9

Preparation of Acetyl-$^{9-32}$Peptide C [SEQ. ID. NO. 48]

Ac-$^{9-32}$Peptide C was prepared as described in Example 8. FAB Mass Spectrometry: (M+H)$^+$ Calculated: 2669; (M+H)$^+$ Found: 2669.

Example 10

Preparation of $^{24}$Ser$^{27}$Val$^{30}$Asn$^{32}$Tyr$^{8-32}$Peptide C [SEQ. ID. NO. 206]

$^{24}$Ser$^{27}$Val$^{30}$Asn$^{32}$Tyr$^{8-32}$Peptide C was prepared as described in Example 1. FAB Mass Spectrometry: (M+H)$^+$ Calculated: 2777.5; (M+H)$^+$ Found: 2777.3.

Example 11

Preparation of $^{24}$Ser$^{27}$Val$^{30}$Asn$^{32}$Tyr$^{9-32}$Peptide C [SEQ. ID. NO. 207]

$^{24}$Ser$^{27}$Val$^{30}$Asn$^{32}$Tyr$^{9-32}$Peptide C was prepared as described in Example 1. FAB Mass Spectrometry: (M+H)$^+$ Calculated: 2677.4; (M+H)$^+$ Found: 2678.4.

Example 12

Preparation of Acetyl-$^{24}$Ser$^{27}$Val$^{30}$Asn$^{32}$Tyr$^{9-32}$Peptide C [SEQ. ID. NO. 207]

Ac-$^{24}$Ser$^{27}$Val$^{30}$Asn$^{32}$Tyr$^{9-32}$Peptide C was prepared as described in Example 8, except that single-coupling cycles were used and the 431 Applied Biosystems peptide synthesizer was used to assemble the two N-terminal residues on the peptide and acetylate the N-terminal of the peptide (cycle g, Boc-chemistry protocol) while it was bound to the resin. FAB Mass Spectrometry: (M+H)$^+$ Calculated: 2720; (M+H)$^+$ Found: 2720.

Example 13

Preparation of Admantyl Acetyl-$^{24}$Ser$^{27}$Val$^{30}$Asn$^{32}$Tyr$^{9-32}$Peptide C [SEQ. ID. NO. 207]

Adamantyl Ac-$^{24}$Ser$^{27}$Val$^{30}$Asn$^{32}$Tyr$^{9-32}$Peptide C was prepared as described in Example 12, except that the N-terminal of the peptide was manually capped, while it was bound to the resin with adamantyl acetic acid, using a four-fold excess and the HOBt-activation. FAB Mass Spectrometry: (M+H)$^+$ Calculated: 2853.5; (M+H)$^+$ Found: 2854.2.

Example 14

Preparation of $^{30}$Asn$^{32}$Tyr$^{8-32}$Peptide C [SEQ. ID. NO. 197]

$^{30}$Asn$^{32}$Tyr$^{8-32}$Peptide C was prepared as described in Example 1. FAB Mass Spectrometry: (M+H)$^+$ Calculated: 2848; (M+H)$^+$ Found: 2848.

Example 15

Preparation of $^{22}$(D)3-(2'Naphthyl)-alanine$^{29}$Ala$^{30}$Asn$^{32}$Tyr$^{22-32}$Peptide C $^{22}$(D)3-(2'Naphthyl)-alanine$^{29}$Ala$^{30}$Asn$^{32}$Tyr$^{22-32}$Peptide C was assembled on an Advanced Chem Tech Synthesizer (Model MPS 350, Louisville, Ky.). The synthesis was done on a 0.016 mmol scale using 4-(2',4'-dimethoxyphenyl-Fmoc-aminomethyl phenoxy resin (Calbiochem, 0.4 mmol/g). The peptide was cleaved from the resin using a mixture of ethanedithiol (0.25 ml), water (0.25 ml), and trifluoroacetic acid (9.5 ml) for 1.5 h with stirring. The peptide resin was filtered and washed with dichloromethane, the filtrates were combined and reduced under vacuum. The peptide was precipitated with ether and the solid collected. Water was used to dissolve the peptide and lyophilization of the filtrates furnished fluffy white peptide. The peptide was purified as described in Example 1. FAB Mass Spectrometry: (M+H)$^+$ Calculated: 1291; (M+H)$^+$ Found: 1291.

Example 16

Preparation of $^{18}$His$^{23}$Phe$^{25}$Ala$^{26}$Ile$^{28}$Ser$^{29}$Ser$^{8-37}$Peptide A [SEQ. ID. NO. 208]

$^{18}$His$^{23}$Phe$^{25}$Ala$^{26}$Ile$^{28}$Ser$^{29}$Ser$^{8-37}$Peptide A was prepared in a similar way as that described in Example 1. FAB Mass Spectrometry: (M+H)$^+$ Calculated: 3183; (M+H)$^+$ Found: 3183.

Example 17

Preparation of $^{18}$His$^{23}$Phe$^{25}$Ala$^{26}$Ile$^{28}$Ser$^{29}$Ser$^{18-37}$Peptide A [SEQ. ID. NO. 209]

$^{18}$His$^{23}$Phe$^{25}$Ala$^{26}$Ile$^{28}$Ser$^{29}$Ser$^{18-37}$Peptide A was prepared in a similar way as that described in Example 1. FAB Mass Spectrometry: (M+H)$^+$ Calculated: 2070; (M+H)$^+$ Found: 2070.

Example 18

Preparation of $^{23}$Phe$^{25}$Ala$^{26}$Ile$^{28}$Ser$^{29}$Ser$^{23-37}$Peptide A [SEQ. ID. NO. 210]

$^{23}$Phe$^{25}$Ala$^{26}$Ile$^{28}$Ser$^{29}$Ser$^{23-37}$Peptide A was prepared in a similar way as that described in Example 1. FAB Mass Spectrometry: (M+H)$^+$ Calculated: 1531; (M+H)$^+$ Found: 1531.

Example 19

Preparation of $^{28}$Ser$^{29}$Ser$^{28-37}$Peptide A [SEQ. ID. NO. 211]

$^{28}$Ser$^{29}$Ser$^{28-37}$Peptide A was prepared in a similar way as that described in Example 1. FAB Mass Spectrometry: (M+H)$^+$ Calculated: 1029; (M+H)$^+$ Found: 1029.

Example 20

Preparation of $^{27}$Tyr$^{28}$Ser$^{29}$Ser$^{27-37}$Peptide A [SEQ. ID. NO. 212]

$^{27}$Tyr$^{28}$Ser$^{29}$Ser$^{27-37}$Peptide A was prepared in a similar way as that described in Example 1. FAB Mass Spectrometry: (M+H)$^+$ Calculated: 1191.5; (M+H)$^+$ Found: 1191.2.

Example 21

Preparation of $^{8-37}$Peptide A [SEQ. ID. NO. 5]

$^{8-37}$Peptide A was prepared in a similar way as that described in Example 1. FAB Mass Spectrometry: (M+H)$^+$ Calculated: 3201; (M+H)$^+$ Found: 3201.

Example 22

Preparation of $^{8-24}$Peptide A [SEQ. ID. NO. 213]

$^{8-24}$Peptide A was prepared in a similar way as that described in Example 1. FAB Mass Spectrometry: (M+H)$^+$ Calculated: 1860; (M+H)$^+$ Found: 1860.

Example 23

Preparation of $^{8-29}$Peptide A [SEQ. ID. NO. 71]

$^{8-24}$Peptide A was prepared in a similar way as that described in Example 1. FAB Mass Spectrometry: (M+H)$^+$ Calculated: 2363.3; (M+H)$^+$ Found: 2364.0.

Example 24

Preparation of $^{8-35}$Peptide A [SEQ. ID. NO. 73]

$^{8-35}$Peptide A was prepared in a similar way as that described in Example 1. FAB Mass Spectrometry: (M+H)$^+$ Calculated: 2936; (M+H)$^+$ Found: 2936.

Example 25

Preparation of $^{18-35}$Peptide A [SEQ. ID. NO. 214]

$^{18-35}$Peptide A was prepared in a similar way as that described in Example 1. FAB Mass Spectrometry: (M+H)$^+$ Calculated: 1822; (M+H)$^+$ Found: 1822.

Example 26

Preparation of $^{8-23,30-37}$Peptide A [SEQ. ID. NO. 215]

$^{8-23,30-37}$Peptide A was prepared in a similar way as that described in Example 1. FAB Mass Spectrometry: (M+H)$^+$ Calculated: 2639.4; (M+H)$^+$ Found: 2640.

Example 27

Preparation of $^{8-29}$Peptide A [SEQ. ID. NO. 71]

$^{8-29}$Peptide A was prepared in a similar way as that described in Example 1. FAB Mass Spectrometry: (M+H)$^+$ Calculated: 2363.3; (M+H)$^+$ Found: 2364.

Example 28

Preparation of $^{27}$Tyr$^{28}$Ser$^{29}$Ser$^{34}$Ala$^{27-37}$Peptide A [SEQ. ID. NO. 216]

$^{27}$Tyr$^{28}$Ser$^{29}$Ser$^{34}$Ala$^{27-37}$Peptide A was prepared in a similar way as that described in Example 15. FAB Mass Spectrometry: (M+H)$^+$ Calculated: 1175.5; (M+H)$^+$ Found: 1175.7.

Example 29

Preparation of $^{18-37}$Peptide B [SEQ. ID. NO. 36]

$^{18-37}$Peptide B was prepared in a similar way as that described in Example 1. FAB Mass Spectrometry: (M+H)$^+$ Calculated: 2077; (M+H)$^+$ Found: 2077.

Example 30

Preparation of $^{9-37}$Peptide B [SEQ. ID. NO. 27]

$^{9-37}$Peptide B was prepared in a similar way as that described in Example 1. FAB Mass Spectrometry: (M+H)$^+$ Calculated: 3026; (M+H)$^+$ Found: 3026.

Example 31

Preparation of $^{11-37}$Peptide B [SEQ. ID. NO. 29]

$^{11-37}$Peptide B was prepared in a similar way as that described in Example 1. FAB Mass Spectrometry: (M+H)$^+$ Calculated: 2788; (M+H)$^+$ Found: 2788.

Example 32

Preparation of $^{27}$Tyr$^{27-37}$Peptide B [SEQ. ID. NO. 217]

$^{27}$Tyr$^{27-37}$Peptide B was prepared in a similar way as that described in Example 1. FAB Mass Spectrometry: (M+H)$^+$ Calculated: 1181.6; (M+H)$^+$ Found: 1181.

Example 33

Preparation of $^{14}$Asp$^{15}$Phe$^{23}$Gly$^{8-37}$Peptide B [SEQ. ID. NO. 218]

$^{14}$Asp$^{15}$Phe$^{23}$Gly$^{8-37}$Peptide B was prepared in a similar way as that described in Example 1, FAB Mass Spectrometry: (M+H)$^+$ Calculated: 3176.6; (M+H)$^+$ Found: 3176.

Example 34

Preparation of $^{14}$Asp$^{15}$Phe$^{23}$Gly$^{8-37}$Peptide B $^{14}$Asp$^{15}$Phe$^{23}$Gly$^{8-37}$Peptide B was prepared in a similar way as that described in Example 1. FAB Mass Spectrometry: (M+H)$^+$ Calculated: 2035.1; (M+H)$^+$ Found: 2035.5.

Example 35

Preparation of (cyclo$^{12,15}$)$^{12,15}$Cys$^{8-37}$Peptide B $^{12,15}$Cys(Acm)$^{8-37}$Peptide B-(resin) is assembled as described in Example 1 using Boc-Cys(Acm) amino acids at positions 12 and 15. The disulfide bond is formed while the peptide is on the resin. The peptide-resin is stirred with a 5% mixture of anisole/TFA (1.7 mM) at −4° to 0° C. Thallic trifluoroacetate (1.2 equivalents with respect to the peptide) is added and the mixture is stirred for 1 hour. The mixture is vacuum filtered and the resin washed with cold ether. The resin is dried under vacuum for at least 2 hours and then cleaved with HF as previously described in Example 1. The peptide, (cyclo$^{12,15}$)$^{12,15}$Cys$^{8-37}$Peptide B is purified as previously described in Example 1.

Example 36

Preparation of (cyclo$^{15,32}$)$^{15}$Lys$^{32}$Asp$^{8-37}$Peptide B [SEQ. ID. NO. 191]

$^{15}$Lys(Fmoc)$^{32}$Asp(OFm)$^{15-37}$Peptide B-(resin) is assembled as described in Example 1 using Boc-Lys(Fmoc) and Boc-Asp(OFm) at positions 15 and 32 respectively. The lactam bond is formed while the peptide is on the resin. The Asp and Lys residues are deprotected by shaking the resin with 20% piperidine in DMF. The peptide-resin (1 equivalent) swollen in a solution of 1.5% DIEA/DMF (1.75 mM) and benzotriazol-1-yl-oxy-tris(dimethylamino)phosphonium hexafluorophosphate (BOP, 6 equivalents) is added.

19

The reaction is shaken for 2 hours. The resin is filtered and washed with DMF. Quantitative ninhydrin analysis is used to determine the extent of the reaction. If the yield is less than 90% the cyclization reaction is repeated. The assembly of (cyclo$^{15,32}$)$^{15}$Lys$^{32}$Asp$^{8-37}$Peptide B-(resin) is completed and (cyclo$^{15,32}$)$^{15}$Lys$^{32}$Asp$^{8-37}$Peptide B furnished by HF cleavage followed by purification as previously described in Example 1.

Example 37

Preparation of Myristylated,$^{22-32}$Peptide C [SEQ. ID. NO. 61]

The peptide was assembled as described in Example 1. The final coupling cycle was done with myristic acid. The peptide was purified as described in Example 1. FAB Mass Spectrometry: (M+H)$^+$ Calculated: 1360; (M+H)$^+$ Found: 1360.

Example 38

Preparation of ($^{5,6}$Aminovaleric Acid)$^{18}$His$^{23}$Phe$^{25}$Ala$^{26}$Ile$^{28}$Ser$^{29}$Ser-Peptide A The peptide was assembled, cyclized, cleaved and purified as described in Examples 1 and 26. Aminovaleric acid was coupled in the place of residues 5 and 6. FAB Mass Spectrometry: (M+H)$^+$ Calculated: 3829.27; (M+H)$^+$ Found: 3829.1.

Example 39

Preparation of ($^{22-32}$Peptide C-Ala)$_2$-Lys-Nle-NH$_2$

This peptide, having a $^{22-32}$Peptide C-Ala fragment bonded to each of the alpha and epsilon amino groups of lysine, is assembled similar to Example 1. The residue Boc-Lys(Boc) is used after coupling norleucine to the resin. After Ala is coupled to both amino groups of the Lys residue, two copies of the sequence $^{22-32}$Peptide C are assembled simultaneously to give ($^{22-32}$Peptide C-Ala)$_2$-Lys-Nle-resin. The peptide-resin is cleaved with HF and purified as described in Example 1 to furnish $^{22-32}$Peptide C-Ala)$_2$-Lys-Nle-NH$_2$.

Example 40

Preparation of [($^{21}$Cys,$^{22-32}$Peptide C-NH$_2$)-SCH$_2$CO-Ala]$_2$-Lys-Nle-NH$_2$ Two peptide modules are assembled, as previously described in Example 1, and reacted together to furnish this branched compound. The branching peptide module is prepared by coupling to resin in the following order: Boc-Nle, Boc-Lys(Boc), Boc-Ala, Bromoacetic acid. The bromoacetic acid is coupled as the symmetric anhydride while the other residues are coupled HOBt-active esters, as previously described. The branched module is cleaved and purified as previously described. The linear module, $^{21}$Cys,$^{22-32}$Peptide C-NH$_2$ is synthesized as described in Example 1 to furnish the free sulfhydryl containing peptide. The linear module is reacted in excess with the branched module in buffered basic solution to furnish the sulfide bonded, branched peptide, [($^{21}$Cys,$^{22-32}$Peptide C-NH$_2$)-SCH$_2$CO-Ala]$_2$-Lys-Nle-NH$_2$.

Example 41

Preparation of [($^{22}$(D)3-(2'Naphthyl)-alanine$^{26}$Cys$^{29}$Ala$^{30}$Asn$^{32}$Tyr $^{22-32}$Peptide C-NH$_2$]$_2$-BMH

20

[($^{22}$(D)3-(2'Naphthyl)-alanine$^{26}$Cys$^{29}$Ala$^{30}$Asn$^{32}$Tyr $^{22-32}$Peptide C-NH$_2$]$_2$-BMH is prepared by synthesizing $^{22}$(D)3-(2'Naphthyl)-alanine$^{26}$Cys$^{29}$Ala$^{30}$Asn$^{32}$Tyr$^{22-32}$Peptide C-NH$_2$ using similar methods as described in Example 1. The peptide (2 equivalents) is reacted with bismaleimidohexane (BMH) in a solution at pH 6.5–7.5 and the resulting mixture is purified to furnish [($^{22}$(D)3-(2'Naphthyl)-alanine$^{26}$Cys$^{29}$Ala$^{30}$Asn$^{32}$Tyr $^{22-32}$Peptide C-NH$_2$)]$_2$-BMH. FAB Mass Spectrometry: (M+H)$^+$ Calculated: 2835; Found: 2835.

Example 42

Preparation of $^{30}$Asn$^{32}$Tyr$^{22-32}$Peptide C [SEQ. ID. NO. 219]

Peptide was prepared in a similar manner as described in Example 15. TOF Mass Spectrometry: (M+H)$^+$ Calculated: 1273.3; Found: 1272.6.

Example 43

Preparation of $^{30}$Arg$^{32}$Tyr$^{22-32}$Peptide C [SEQ. ID. NO. 220]

Peptide was prepared in a similar manner as described in Example 15. TOF Mass Spectrometry: (M+H)$^+$ Calculated: 1315.4; Found: 1286.8.

Example 44

Preparation of $^{30}$Lys$^{32}$Tyr$^{22-32}$Peptide C [SEQ. ID. NO. 221]

Peptide was prepared in a similar manner as described in Example 15. TOF Mass Spectrometry: (M+H)$^+$ Calculated: 1287.4; Found: 1286.6.

Example 45

Preparation of $^{27}$Val$^{30}$Asn$^{32}$Tyr$^{22-32}$Peptide C [SEQ. ID. NO. 222]

Peptide was prepared in a similar manner as described in Example 15. TOF Mass Spectrometry: (M+H)$^+$ Calculated: 1271.4; Found: 1270.5.

Example 46

Preparation of Acetyl-$^{30}$Asn$^{32}$Tyr$^{8-32}$Peptide C [SEQ. ID. NO. 197]

Peptide was prepared in a similar manner as described in Example 1. Acetylation of the N-terminus was accomplished by the ENDCAP program using acetic anhydride and diisopropylethylamine. FAB Mass Spectrometry: (M+H)$^+$ Calculated: 2848.2; Found: 2848.2.

Example 47

Preparation of Acetyl-$^{11,18}$Arg$^{15}$Leu$^{30}$Asn$^{32}$Tyr$^{9-32}$Peptide C [SEQ. ID. NO. 200]

Peptide was assembled on 4-(2',4'-dimethoxyphenyl)-Fmoc aminomethyl phenoxy resin (Novabiochem, 0.44 mmole/g) using Fmoc-protected amino acids from Applied Biosystems, Inc. Single-coupling cycles were used throughout the synthesis and Fast Moc (HBTU activation) chemistry. Acetylation was accomplished by the ENDCAP program using acetic anhydride. The completed peptide resin was deprotected and cleaved using a mixture of phenol (0.75 g), ethanedithiol (0.25 ml), thioanisole (0.5 ml), water (0.5 ml) and trifluoroacetic acid (10 ml) according to standard methods (Introduction to Cleavage Techniques, Applied Biosystems, Inc.). FAB Mass Spectrometry: $(M+H)^+$ Calculated: 2832.2; Found: 2831.3).

Example 48

Preparation of Acetyl-$^{11,18}$Arg$^{30}$Asn$^{32}$Tyr$^{9-32}$Peptide C [SEQ. ID. NO. 201]

Peptide was prepared in a similar manner as described in Example 47. FAB Mass Spectrometry: $(M+H)^+$ Calculated: 2848.1; Found: 2847.5.

Example 49

Preparation of Acetyl-$^{18}$Arg$^{30}$Asn$^{32}$Tyr$^{9-32}$Peptide C [SEQ. ID. NO. 202]

Peptide was prepared in a similar manner as described in Example 47. FAB Mass Spectrometry: $(M+H)^+$ Calculated: 2820.1; Found: 2819.3.

Example 50

Preparation of $^{27}$Tyr$^{28}$Pro$^{29}$Arg$^{34}$Ala$^{27-37}$Peptide A [SEQ. ID. NO. 223]

Peptide was prepared in a similar manner as described in Example 15. TOF Mass Spectrometry: $(M+H)^+$ Calculated: 1255.4; Found: 1255.

Example 51

Preparation of $^{27}$Tyr$^{28}$Pro$^{29}$Arg$^{32}$Thr$^{34}$Ala$^{27-37}$Peptide A [SEQ. ID. NO. 224]

Peptide was prepared in a similar manner as described in Example 15. FAB Mass Spectrometry: $(M+H)^+$ Calculated: 1257.3.

Example 52

Preparation of $^{22}$(D)3-(2'Naphthyl)-alanine$^{29}$Ala$^{30}$Phe$^{32}$Tyr$^{22-32}$Peptide C Peptide was prepared in a similar manner as described in Example 15. TOF Mass Spectrometry: $(M+H)^+$ Calculated: 1324.5; Found: 1324.9.

Example 53

Preparation of $^{22}$(D)3-(2'Naphthyl)-alanine$^{29}$Ala$^{30}$Asn$^{32}$Tyr-$^{22-32}$Peptide C Peptide was prepared in a similar manner as described in Example 15. FAB Mass Spectrometry: $(M+H)^+$ Calculated: 1291.6; Found: 1291.3.

Example 54

Preparation of $^{22}$(D)3-(2'Naphthyl)-alanine$^{27}$Val$^{29}$Ala$^{30}$Asn $^{32}$Tyr-$^{22-32}$Peptide C Peptide was prepared in a similar manner as described in Example 15. TOF Mass Spectrometry: $(M+H)^+$ Calculated: 1289.4; Found: 1290.4.

---

We claim:

1. An amylin antagonist peptide which is an N-terminal deletion peptide of Peptide A, modified Peptide A, Peptide B, modified Peptide B, Peptide C, or modified Peptide C, wherein at least the first two to seven N-terminal amino acid residues of Peptide A or modified Peptide A have been deleted, at least the first eight N-terminal amino acid residues of Peptide B or modified Peptide B have been deleted, and at least the first two to seven N-terminal amino acid residues of Peptide C or modified Peptide C have been deleted, each such amylin antagonist peptide optionally having an acetylated N-terminal amino acid, a carboxy-amidated C-terminal amino acid, or both.

2. An amylin antagonist peptide according to claim 1 having an $IC_{50}$ in an amylin receptor assay of less than about 5 nM and an $IC_{50}$ in a soleus muscle antagonist assay of less than about 1 µM.

3. An amylin antagonist peptide according to claim 1 which is a deletion peptide based on Peptide C or modified Peptide C.

4. An amylin antagonist peptide according to claim 3 wherein said deletion peptide based on Peptide C or modified Peptide C is $^{8-32}$Peptide C or modified $^{8-32}$Peptide C or a peptide having successive N-terminal deletions thereof up to and including $^{24-32}$Peptide C or modified $^{24-32}$Peptide C.

5. An amylin antagonist peptide according to claim 4 wherein modified Peptide C is a peptide having at least one amino acid substitution selected from the group $^{26}$Ala, $^{26}$Asp, $^{26}$Gln, $^{26}$Glu, $^{27}$Val, $^{29}$Ala, $^{29}$Gly, $^{30}$Asn, $^{30}$Lys, $^{30}$Arg, $^{30}$Ala, $^{30}$Phe, $^{32}$Tyr, $^{32}$Hyp, $^{32}$Thr, $^{32}$Phe or $^{32}$Hydroxyproline.

6. An amylin antagonist peptide according to claim 5 which is modified $^{8-32}$Peptide C, modified $^{9-32}$Peptide C, modified $^{22-32}$Peptide C or modified $^{24-32}$Peptide C.

7. An amylin antagonist peptide according to claim 5 which is modified $^{8-32}$Peptide C or modified $^{9-32}$Peptide C, said modified Peptides not having a C-terminal $NH_2$ group.

8. An amylin antagonist peptide according to claim 5 which is modified $^{22-32}$Peptide C or modified $^{24-32}$Peptide C, said modified Peptides not having a C-terminal $NH_2$ group.

9. An amylin antagonist peptide according to claim 3 which is $^{9-32}$Peptide C or modified $^{9-32}$Peptide C.

10. An amylin antagonist peptide according to claim 9 wherein modified Peptide C is a peptide having at least one amino acid substitution selected from the group consisting of $^{11}$Arg, $^{15}$Leu, $^{18}$Arg, $^{30}$Asn, and $^{32}$Tyr.

11. An amylin antagonist peptide according to claim 3 which is from about 9 to about 11 amino acids long.

12. An amylin antagonist peptide according to claim 11 which is $^{22-32}$Peptide C, modified $^{23-32}$Peptide C, $^{24-32}$Peptide C or modified $^{26-32}$Peptide C.

13. An amylin antagonist peptide according to claim 12 having at least one amino acid substitution selected from the group consisting of $^{22}$D-Nal, $^{22}$L-Nal, $^{26}$D-Asp, $^{26}$L-Asp, $^{27}$Val, $^{30}$Asn, $^{30}$Phe, $^{30}$Lys, $^{30}$Arg, $^{32}$Tyr and $^{32}$Hydroxyproline.

14. An amylin antagonist peptide which is an N-terminal deletion peptide of Peptide C having at least amino acids 1 to 7 deleted and optionally including substitutions in amino acid sequence selected from: at residue 11, replacing Lys with Arg; at residue 15, replacing Glu with Phe; at residue 18, replacing Lys with Arg; at residue 26, replacing Asn with Ala, Asp, Gln or Glu; at residue 27, replacing Thr with Val; at residue 29, replacing Ser with Ala or Gly; at residue 30, replacing Glu with Asn, Lys, Arg or Ala; and at residue 32, replacing Pro with Tyr, Phe or Hydroxyproline; and an optionally having an acetylated N-terminal amino acid, a carboxy-amidated C-terminal amine acid, or both.

15. An amylin antagonist peptide according to claim 14 having the amino acid sequence Ac-$^{11}$Arg$^{15}$Leu$^{18}$Arg$^{30}$Asn$^{32}$Tyr$^{9-32}$Peptide C.

16. An amylin antagonist peptide according to claim 14 having the amino acid sequence Ac-$^{11}$Arg$^{18}$Arg$^{30}$Asn$^{32}$Tyr$^{9-32}$Peptide C.

17. An amylin antagonist peptide according to claim 14.

18. An amylin antagonist peptide according to claim 14 having the amino acid sequence Ac-$^{30}$Asn$^{32}$Tyr$^{8-32}$Peptide C.

19. An amylin antagonist peptide of claim 1 having the amino acid sequence X-$Xaa_1$-Leu-Gly-$Xaa_2$-Leu-Ser-Gln-$Xaa_3$-Leu-His-$Xaa_4$-Leu-Gln-Thr-Tyr-Pro-Arg-Thr-Asn-$Xaa_5$-Gly-$Xaa_6$-$Xaa_7$-Thr-$Xaa_8$-Y wherein X is lower acyl or hydrogen; $Xaa_1$ is Val, Ala or absent; $Xaa_2$ is Lys, Arg or Orn; $Xaa_3$ is Glu, Asp, Leu or Phe; $Xaa_4$ is Lys, Arg or Orn; $Xaa_5$ is Thr or Val; $Xaa_6$ is Ser or Ala; $Xaa_7$ is Gly, Asn, Lys, Arg or Orn; $Xaa_8$ is Pro, Tyr or Phe; and Y is —OH or —$NH_2$.

20. An amylin antagonist peptide of claim 19 wherein $Xaa_5$ is Thr and $Xaa_6$ is Ser.

21. An amylin antagonist peptide of claim 20 wherein $Xaa_7$ is Asn and $Xaa_8$ is Tyr.

22. An amylin antagonist peptide of claim 21 wherein $Xaa_3$ is Glu.

23. An amylin antagonist peptide of claim 22 wherein $Xaa_1$ is Val.

24. An amylin antagonist peptide of claim 22 wherein $Xaa_1$ is absent.

* * * * *

SEQUENCE LISTING ( 1 ) GENERAL INFORMATION:

( i i i ) NUMBER OF SEQUENCES: 227

( 2 ) INFORMATION FOR SEQ ID NO: 1:

( i ) SEQUENCE CHARACTERISTICS:
        ( A ) LENGTH: 37 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 1:

```
Lys  Cys  Asn  Thr  Ala  Thr  Cys  Ala  Thr  Gln  Arg  Leu  Ala  Asn
                    5                        10
Phe  Leu  Val  His  Ser  Ser  Asn  Asn  Phe  Gly  Ala  Ile  Leu  Ser
15                  20                       25
Ser  Thr  Asn  Val  Gly  Ser  Asn  Thr  Tyr
     30                  35
```

( 2 ) INFORMATION FOR SEQ ID NO: 2:

( i ) SEQUENCE CHARACTERISTICS:
        ( A ) LENGTH: 37 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 2:

Lys  Cys  Asn  Thr  Ala  Thr  Cys  Ala  Thr  Gln  Arg  Leu  Ala  Asn
                    5                        10
Phe  Leu  Val  Arg  Ser  Ser  Asn  Asn  Leu  Gly  Pro  Val  Leu  Pro
15                       20                       25
Pro  Thr  Asn  Val  Gly  Ser  Asn  Thr  Tyr
     30                       35

( 2 ) INFORMATION FOR SEQ ID NO: 3:

( i ) SEQUENCE CHARACTERISTICS:
          ( A ) LENGTH: 37 AMINO ACIDS
          ( B ) TYPE: AMINO ACID
          ( D ) TOPOLOGY: LINEAR ( i i ) MOLECULE TYPE: PEPTIDE ( i x ) FEATURE:
          ( D ) OTHER INFORMATION:

( x i ) SEQUENCE DESCRIPTION: SEQ ID NO: 3:

Ala  Cys  Asp  Thr  Ala  Thr  Cys  Val  Thr  His  Arg  Leu  Ala  Gly
                    5                        10
Leu  Leu  Ser  Arg  Ser  Gly  Gly  Val  Val  Lys  Asn  Asn  Phe  Val
15                       20                       25
Pro  Thr  Asn  Val  Gly  Ser  Lys  Ala  Phe
     30                       35

( 2 ) INFORMATION FOR SEQ ID NO: 4:

( i ) SEQUENCE CHARACTERISTICS:
          ( A ) LENGTH: 32 AMINO ACIDS
          ( B ) TYPE: AMINO ACID
          ( D ) TOPOLOGY: LINEAR ( i i ) MOLECULE TYPE: PEPTIDE ( i x ) FEATURE:
          ( D ) OTHER INFORMATION:

( x i ) SEQUENCE DESCRIPTION: SEQ ID NO: 4:

Cys  Ser  Asn  Leu  Ser  Thr  Cys  Val  Leu  Gly  Lys  Leu  Ser  Gln
                    5                        10
Glu  Leu  His  Lys  Leu  Gln  Thr  Tyr  Pro  Arg  Thr  Asn  Thr  Gly
15                       20                       25
Ser  Gly  Thr  Pro
     30

( 2 ) INFORMATION FOR SEQ ID NO: 5:

( i ) SEQUENCE CHARACTERISTICS:
          ( A ) LENGTH: 30 AMINO ACIDS
          ( B ) TYPE: AMINO ACID
          ( D ) TOPOLOGY: LINEAR ( i i ) MOLECULE TYPE: PEPTIDE ( i x ) FEATURE:
          ( D ) OTHER INFORMATION:

( x i ) SEQUENCE DESCRIPTION: SEQ ID NO: 5:

Ala  Thr  Gln  Arg  Leu  Ala  Asn  Phe  Leu  Val  Arg  Ser  Ser  Asn
                    5                        10
Asn  Leu  Gly  Pro  Val  Leu  Pro  Thr  Asn  Val  Gly  Ser  Asn
15                       20                       25

Thr Tyr
    30

( 2 ) INFORMATION FOR SEQ ID NO: 6:

( i ) SEQUENCE CHARACTERISTICS:
        ( A ) LENGTH: 29 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 6:

Thr Gln Arg Leu Ala Asn Phe Leu Val Arg Ser Ser Asn Asn
                  5                   10
Leu Gly Pro Val Leu Pro Pro Thr Asn Val Gly Ser Asn Thr
15                  20                  25
Tyr ( 2 ) INFORMATION FOR SEQ ID NO: 7:

( i ) SEQUENCE CHARACTERISTICS:
        ( A ) LENGTH: 28 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 7:

Gln Arg Leu Ala Asn Phe Leu Val Arg Ser Ser Asn Asn Leu
                  5                   10
Gly Pro Val Leu Pro Pro Thr Asn Val Gly Ser Asn Thr Tyr
15                  20                  25

( 2 ) INFORMATION FOR SEQ ID NO: 8:

( i ) SEQUENCE CHARACTERISTICS:
        ( A ) LENGTH: 27 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 8:

Arg Leu Ala Asn Phe Leu Val Arg Ser Ser Asn Asn Leu Gly
                  5                   10
Pro Val Leu Pro Pro Thr Asn Val Gly Ser Asn Thr Tyr
15                  20                  25

( 2 ) INFORMATION FOR SEQ ID NO: 9:

( i ) SEQUENCE CHARACTERISTICS:
        ( A ) LENGTH: 26 AMINO ACIDS
        ( B ) TYPE: AMINO ACID
        ( D ) TOPOLOGY: LINEAR ( i i ) MOLECULE TYPE: PEPTIDE ( i x ) FEATURE:

( D ) OTHER INFORMATION:

( x i ) SEQUENCE DESCRIPTION: SEQ ID NO: 9:

Leu Ala Asn Phe Leu Val Arg Ser Ser Asn Asn Leu Gly Pro
                 5                       10
Val Leu Pro Pro Thr Asn Val Gly Ser Asn Thr Tyr
15                   20                  25

( 2 ) INFORMATION FOR SEQ ID NO: 10:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 10:

Ala Asn Phe Leu Val Arg Ser Ser Asn Asn Leu Gly Pro Val
                 5                       10
Leu Pro Pro Thr Asn Val Gly Ser Asn Thr Tyr
15                   20                  25

( 2 ) INFORMATION FOR SEQ ID NO: 11:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 11:

Asn Phe Leu Val Arg Ser Ser Asn Asn Leu Gly Pro Val Leu
                 5                       10
Pro Pro Thr Asn Val Gly Ser Asn Thr Tyr
15                   20

( 2 ) INFORMATION FOR SEQ ID NO: 12:

( i ) SEQUENCE CHARACTERISTICS:
        ( A ) LENGTH: 23 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 12:

Phe Leu Val Arg Ser Ser Asn Asn Leu Gly Pro Val Leu Pro
                 5                       10
Pro Thr Asn Val Gly Ser Asn Thr Tyr
15                   20

( 2 ) INFORMATION FOR SEQ ID NO: 13:

( i ) SEQUENCE CHARACTERISTICS:
        ( A ) LENGTH: 22 AMINO ACIDS
        ( B ) TYPE: AMINO ACID
        ( D ) TOPOLOGY: LINEAR (ii) MOLECULE TYPE: PEPTIDE (ix) FEATURE:
    (D) OTHER INFORMATION:

(xi) SEQUENCE DESCRIPTION: SEQ ID NO: 13:

Leu Val Arg Ser Ser Asn Asn Leu Gly Pro Val Leu Pro Pro
                  5                        10

Thr Asn Val Gly Ser Asn Thr Tyr
15                  20

(2) INFORMATION FOR SEQ ID NO: 14:

(i) SEQUENCE CHARACTERISTICS:
        (A) LENGTH: 21 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 14:

Val Arg Ser Ser Asn Asn Leu Gly Pro Val Leu Pro Pro Thr
                5                        10

Asn Val Gly Ser Asn Thr Tyr
15             20

(2) INFORMATION FOR SEQ ID NO: 15:

(i) SEQUENCE CHARACTERISTICS:
        (A) LENGTH: 20 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 15:

Arg Ser Ser Asn Asn Leu Gly Pro Val Leu Pro Pro Thr Asn
            5                        10

Val Gly Ser Asn Thr Tyr
15            20

(2) INFORMATION FOR SEQ ID NO: 16:

(i) SEQUENCE CHARACTERISTICS:
        (A) LENGTH: 19 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 16:

Ser Ser Asn Asn Leu Gly Pro Val Leu Pro Pro Thr Asn Val
          5                      10

Gly Ser Asn Thr Tyr
15

(2) INFORMATION FOR SEQ ID NO: 17:

(i) SEQUENCE CHARACTERISTICS:
　　(A) LENGTH: 18 AMINO ACIDS
　　(B) TYPE: AMINO ACID
　　(D) TOPOLOGY: LINEAR (i i) MOLECULE TYPE: PEPTIDE (i x) FEATURE:
　　(D) OTHER INFORMATION:

(x i) SEQUENCE DESCRIPTION: SEQ ID NO: 17:

Ser Asn Asn Leu Gly Pro Val Leu Pro Pro Thr Asn Val Gly
　　　　　　　　　5　　　　　　　　　　　　　　　10
Ser Asn Thr Tyr
15

(2) INFORMATION FOR SEQ ID NO: 18:

(i) SEQUENCE CHARACTERISTICS:
　　　　(A) LENGTH: 17 AMINO ACIDS
　　　　(B) TYPE: AMINO ACID
　　　　(D) TOPOLOGY: LINEAR (i i) MOLECULE TYPE: PEPTIDE (i x) FEATURE:
　　　　(D) OTHER INFORMATION:

(x i) SEQUENCE DESCRIPTION: SEQ ID NO: 18:

Asn Asn Leu Gly Pro Val Leu Pro Pro Thr Asn Val Gly Ser
　　　　　　　　5　　　　　　　　　　　　　　　10
Asn Thr Tyr
15

(2) INFORMATION FOR SEQ ID NO: 19:

(i) SEQUENCE CHARACTERISTICS:
　　　　(A) LENGTH: 16 AMINO ACIDS
　　　　(B) TYPE: AMINO ACID
　　　　(D) TOPOLOGY: LINEAR (i i) MOLECULE TYPE: PEPTIDE (i x) FEATURE:
　　　　(D) OTHER INFORMATION:

(x i) SEQUENCE DESCRIPTION: SEQ ID NO: 19:

Asn Leu Gly Pro Val Leu Pro Pro Thr Asn Val Gly Ser Asn
　　　　　　　5　　　　　　　　　　　　　　　10
Thr Tyr
15

(2) INFORMATION FOR SEQ ID NO: 20:

(i) SEQUENCE CHARACTERISTICS:
　　　　(A) LENGTH: 15 AMINO ACIDS
　　　　(B) TYPE: AMINO ACID
　　　　(D) TOPOLOGY: LINEAR (i i) MOLECULE TYPE: PEPTIDE (i x) FEATURE:
　　　　(D) OTHER INFORMATION:

(x i) SEQUENCE DESCRIPTION: SEQ ID NO: 20:

Leu Gly Pro Val Leu Pro Pro Thr Asn Val Gly Ser Asn Thr
　　　　　5　　　　　　　　　　　　　　　10
Tyr
15

( 2 ) INFORMATION FOR SEQ ID NO: 21:

( i ) SEQUENCE CHARACTERISTICS:
        ( A ) LENGTH: 14 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 21:

Gly Pro Val Leu Pro Pro Thr Asn Val Gly Ser Asn Thr Tyr
                5                      10

( 2 ) INFORMATION FOR SEQ ID NO: 22:

( i ) SEQUENCE CHARACTERISTICS:
        ( A ) LENGTH: 13 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 22:

Pro Val Leu Pro Pro Thr Asn Val Gly Ser Asn Thr Tyr
              5                    10

( 2 ) INFORMATION FOR SEQ ID NO: 23:

( i ) SEQUENCE CHARACTERISTICS:
        ( A ) LENGTH: 12 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 23:

Val Leu Pro Pro Thr Asn Val Gly Ser Asn Thr Tyr
          5                  10

( 2 ) INFORMATION FOR SEQ ID NO: 24:

( i ) SEQUENCE CHARACTERISTICS:
        ( A ) LENGTH: 11 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 24:

Leu Pro Pro Thr Asn Val Gly Ser Asn Thr Tyr
      5                  10

( 2 ) INFORMATION FOR SEQ ID NO: 25:

( i ) SEQUENCE CHARACTERISTICS:
        ( A ) LENGTH: 10 AMINO ACIDS
        ( B ) TYPE: AMINO ACID
        ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 25:

Pro Pro Thr Asn Val Gly Ser Asn Thr Tyr
                5                   10

( 2 ) INFORMATION FOR SEQ ID NO: 26:

( i ) SEQUENCE CHARACTERISTICS:
            ( A ) LENGTH: 30 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 26:

Val Thr His Arg Leu Ala Gly Leu Leu Ser Arg Ser Gly Gly
                5                       10
Val Val Lys Asn Asn Phe Val Pro Thr Asn Val Gly Ser Lys
15                  20                      25
Ala Phe
    30

( 2 ) INFORMATION FOR SEQ ID NO: 27:

( i ) SEQUENCE CHARACTERISTICS:
            ( A ) LENGTH: 29 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 27:

Thr His Arg Leu Ala Gly Leu Leu Ser Arg Ser Gly Gly Val
                5                       10
Val Lys Asn Asn Phe Val Pro Thr Asn Val Gly Ser Lys Ala
15                  20                      25
Phe ( 2 ) INFORMATION FOR SEQ ID NO: 28:

( i ) SEQUENCE CHARACTERISTICS:
            ( A ) LENGTH: 28 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 28:

His Arg Leu Ala Gly Leu Leu Ser Arg Ser Gly Gly Val Val
                5                       10
Lys Asn Asn Phe Val Pro Thr Asn Val Gly Ser Lys Ala Phe
15                  20                      25

( 2 ) INFORMATION FOR SEQ ID NO: 29:

( i ) SEQUENCE CHARACTERISTICS:
        ( A ) LENGTH: 27 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 29:

```
Arg  Leu  Ala  Gly  Leu  Leu  Ser  Arg  Ser  Gly  Gly  Val  Val  Lys
                    5                        10
Asn  Asn  Phe  Val  Pro  Thr  Asn  Val  Gly  Ser  Lys  Ala  Phe
15                       20                       25
```

( 2 ) INFORMATION FOR SEQ ID NO: 30:

( i ) SEQUENCE CHARACTERISTICS:
        ( A ) LENGTH: 26 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 30:

```
Leu  Ala  Gly  Leu  Leu  Ser  Arg  Ser  Gly  Gly  Val  Val  Lys  Asn
                    5                        10
Asn  Phe  Val  Pro  Thr  Asn  Val  Gly  Ser  Lys  Ala  Phe
15                       20                       25
```

( 2 ) INFORMATION FOR SEQ ID NO: 31:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 31:

```
Ala  Gly  Leu  Leu  Ser  Arg  Ser  Gly  Gly  Val  Val  Lys  Asn  Asn
                    5                        10
Phe  Val  Pro  Thr  Asn  Val  Gly  Ser  Lys  Ala  Phe
15                       20                       25
```

( 2 ) INFORMATION FOR SEQ ID NO: 32:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 32:

```
Gly  Leu  Leu  Ser  Arg  Ser  Gly  Gly  Val  Val  Lys  Asn  Asn  Phe
                    5                        10
```

Val Pro Thr Asn Val Gly Ser Lys Ala Phe
15                  20

( 2 ) INFORMATION FOR SEQ ID NO: 33:

( i ) SEQUENCE CHARACTERISTICS:
      ( A ) LENGTH: 23 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:

( x i ) SEQUENCE DESCRIPTION: SEQ ID NO: 33:

Leu Leu Ser Arg Ser Gly Gly Val Val Lys Asn Asn Phe Val
            5                         10

Pro Thr Asn Val Gly Ser Lys Ala Phe
15                  20

( 2 ) INFORMATION FOR SEQ ID NO: 34:

( i ) SEQUENCE CHARACTERISTICS:
      ( A ) LENGTH: 22 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:

( x i ) SEQUENCE DESCRIPTION: SEQ ID NO: 34:

Leu Ser Arg Ser Gly Gly Val Val Lys Asn Asn Phe Val Pro
            5                         10

Thr Asn Val Gly Ser Lys Ala Phe
15                  20

( 2 ) INFORMATION FOR SEQ ID NO: 35:

( i ) SEQUENCE CHARACTERISTICS:
      ( A ) LENGTH: 21 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:

( x i ) SEQUENCE DESCRIPTION: SEQ ID NO: 35:

Ser Arg Ser Gly Gly Val Val Lys Asn Asn Phe Val Pro Thr
            5                         10

Asn Val Gly Ser Lys Ala Phe
15                  20

( 2 ) INFORMATION FOR SEQ ID NO: 36:

( i ) SEQUENCE CHARACTERISTICS:
      ( A ) LENGTH: 20 AMINO ACIDS
      ( B ) TYPE: AMINO ACID
      ( D ) TOPOLOGY: LINEAR ( i i ) MOLECULE TYPE: PEPTIDE ( i x ) FEATURE:
      ( D ) OTHER INFORMATION:

( x i ) SEQUENCE DESCRIPTION: SEQ ID NO: 36:

```
Arg  Ser  Gly  Gly  Val  Val  Lys  Asn  Asn  Phe  Val  Pro  Thr  Asn
               5                        10

Val  Gly  Ser  Lys  Ala  Phe
15                   20
```

( 2 ) INFORMATION FOR SEQ ID NO: 37:

( i ) SEQUENCE CHARACTERISTICS:
        ( A ) LENGTH: 19 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 37:

```
Ser  Gly  Gly  Val  Val  Lys  Asn  Asn  Phe  Val  Pro  Thr  Asn  Val
               5                        10

Gly  Ser  Lys  Ala  Phe
15
```

( 2 ) INFORMATION FOR SEQ ID NO: 38:

( i ) SEQUENCE CHARACTERISTICS:
        ( A ) LENGTH: 18 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 38:

```
Gly  Gly  Val  Val  Lys  Asn  Asn  Phe  Val  Pro  Thr  Asn  Val  Gly
               5                        10

Ser  Lys  Ala  Phe
15
```

( 2 ) INFORMATION FOR SEQ ID NO: 39:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 39:

```
Gly  Val  Val  Lys  Asn  Asn  Phe  Val  Pro  Thr  Asn  Val  Gly  Ser
               5                        10

Lys  Ala  Phe
15
```

( 2 ) INFORMATION FOR SEQ ID NO: 40:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 40:

Val Val Lys Asn Asn Phe Val Pro Thr Asn Val Gly Ser Lys
                    5                           10
Ala Phe
15

( 2 ) INFORMATION FOR SEQ ID NO: 41:

( i ) SEQUENCE CHARACTERISTICS:
    ( A ) LENGTH: 15 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 41:

Val Lys Asn Asn Phe Val Pro Thr Asn Val Gly Ser Lys Ala
                5                       10
Phe
15

( 2 ) INFORMATION FOR SEQ ID NO: 42:

( i ) SEQUENCE CHARACTERISTICS:
    ( A ) LENGTH: 14 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 42:

Lys Asn Asn Phe Val Pro Thr Asn Val Gly Ser Lys Ala Phe
                    5                       10

( 2 ) INFORMATION FOR SEQ ID NO: 43:

( i ) SEQUENCE CHARACTERISTICS:
    ( A ) LENGTH: 13 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 43:

Asn Asn Phe Val Pro Thr Asn Val Gly Ser Lys Ala Phe
                5                   10

( 2 ) INFORMATION FOR SEQ ID NO: 44:

( i ) SEQUENCE CHARACTERISTICS:
    ( A ) LENGTH: 12 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 44:

Asn Phe Val Pro Thr Asn Val Gly Ser Lys Ala Phe
            5                   10

( 2 ) INFORMATION FOR SEQ ID NO: 45:

( i ) SEQUENCE CHARACTERISTICS:
  ( A ) LENGTH: 11 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 45:

Phe Val Pro Thr Asn Val Gly Ser Lys Ala Phe
            5                   10

( 2 ) INFORMATION FOR SEQ ID NO: 46:

( i ) SEQUENCE CHARACTERISTICS:
  ( A ) LENGTH: 10 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 46:

Val Pro Thr Asn Val Gly Ser Lys Ala Phe
            5                   10

( 2 ) INFORMATION FOR SEQ ID NO: 47:

( i ) SEQUENCE CHARACTERISTICS:
  ( A ) LENGTH: 25 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 47:

Val Leu Gly Lys Leu Ser Gln Glu Leu His Lys Leu Gln Thr
            5                   10

Tyr Pro Arg Thr Asn Thr Gly Ser Gly Thr Pro
15              20              25

( 2 ) INFORMATION FOR SEQ ID NO: 48:

( i ) SEQUENCE CHARACTERISTICS:
  ( A ) LENGTH: 24 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 48:

Leu Gly Lys Leu Ser Gln Glu Leu His Lys Leu Gln Thr Tyr
            5                   10

```
Pro Arg Thr Asn Thr Gly Ser Gly Thr Pro
15                  20
```

( 2 ) INFORMATION FOR SEQ ID NO: 49:

( i ) SEQUENCE CHARACTERISTICS:
    ( A ) LENGTH: 23 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 49:

```
Gly Lys Leu Ser Gln Glu Leu His Lys Leu Gln Thr Tyr Pro
                5                   10

Arg Thr Asn Thr Gly Ser Gly Thr Pro
15              20
```

( 2 ) INFORMATION FOR SEQ ID NO: 50:

( i ) SEQUENCE CHARACTERISTICS:
    ( A ) LENGTH: 22 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 50:

```
Lys Leu Ser Gln Glu Leu His Lys Leu Gln Thr Tyr Pro Arg
                5                   10

Thr Asn Thr Gly Ser Gly Thr Pro
15              20
```

( 2 ) INFORMATION FOR SEQ ID NO: 51:

( i ) SEQUENCE CHARACTERISTICS:
    ( A ) LENGTH: 21 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 51:

```
Leu Ser Gln Glu Leu His Lys Leu Gln Thr Tyr Pro Arg Thr
            5                   10

Asn Thr Gly Ser Gly Thr Pro
15              20
```

( 2 ) INFORMATION FOR SEQ ID NO: 52:

( i ) SEQUENCE CHARACTERISTICS:
    ( A ) LENGTH: 20 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 52:

Ser Gln Glu Leu His Lys Leu Gln Thr Tyr Pro Arg Thr Asn
                      5                  10
Thr Gly Ser Gly Thr Pro
15                   20

( 2 ) INFORMATION FOR SEQ ID NO: 53:

( i ) SEQUENCE CHARACTERISTICS:
        ( A ) LENGTH: 19 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 53:

Gln Glu Leu His Lys Leu Gln Thr Tyr Pro Arg Thr Asn Thr
                  5                  10
Gly Ser Gly Thr Pro
15

( 2 ) INFORMATION FOR SEQ ID NO: 54:

( i ) SEQUENCE CHARACTERISTICS:
        ( A ) LENGTH: 18 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 54:

Glu Leu His Lys Leu Gln Thr Tyr Pro Arg Thr Asn Thr Gly
              5                  10
Ser Gly Thr Pro
15

( 2 ) INFORMATION FOR SEQ ID NO: 55:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 55:

Leu His Lys Leu Gln Thr Tyr Pro Arg Thr Asn Thr Gly Ser
             5                  10
Gly Thr Pro
15

( 2 ) INFORMATION FOR SEQ ID NO: 56:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 56:

His Lys Leu Gln Thr Tyr Pro Arg Thr Asn Thr Gly Ser Gly
                5                           10
Thr Pro
15

( 2 ) INFORMATION FOR SEQ ID NO: 57:

( i ) SEQUENCE CHARACTERISTICS:
        ( A ) LENGTH: 15 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 57:

Lys Leu Gln Thr Tyr Pro Arg Thr Asn Thr Gly Ser Gly Thr
                5                           10
Pro
15

( 2 ) INFORMATION FOR SEQ ID NO: 58:

( i ) SEQUENCE CHARACTERISTICS:
        ( A ) LENGTH: 14 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 58:

Leu Gln Thr Tyr Pro Arg Thr Asn Thr Gly Ser Gly Thr Pro
                5                           10

( 2 ) INFORMATION FOR SEQ ID NO: 59:

( i ) SEQUENCE CHARACTERISTICS:
        ( A ) LENGTH: 13 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 59:

Gln Thr Tyr Pro Arg Thr Asn Thr Gly Ser Gly Thr Pro
                5                       10

( 2 ) INFORMATION FOR SEQ ID NO: 60:

( i ) SEQUENCE CHARACTERISTICS:
        ( A ) LENGTH: 12 AMINO ACIDS
        ( B ) TYPE: AMINO ACID
        ( D ) TOPOLOGY: LINEAR ( i i ) MOLECULE TYPE: PEPTIDE ( i x ) FEATURE:

(D) OTHER INFORMATION:

(x i) SEQUENCE DESCRIPTION: SEQ ID NO: 60:

Thr Tyr Pro Arg Thr Asn Thr Gly Ser Gly Thr Pro
                  5                   10

(2) INFORMATION FOR SEQ ID NO: 61:

(i) SEQUENCE CHARACTERISTICS:
        (A) LENGTH: 11 AMINO ACIDS
        (B) TYPE: AMINO ACID
        (D) TOPOLOGY: LINEAR (i i) MOLECULE TYPE: PEPTIDE (i x) FEATURE:
        (D) OTHER INFORMATION:

(x i) SEQUENCE DESCRIPTION: SEQ ID NO: 61:

Tyr Pro Arg Thr Asn Thr Gly Ser Gly Thr Pro
              5                   10

(2) INFORMATION FOR SEQ ID NO: 62:

(i) SEQUENCE CHARACTERISTICS:
        (A) LENGTH: 10 AMINO ACIDS
        (B) TYPE: AMINO ACID
        (D) TOPOLOGY: LINEAR (i i) MOLECULE TYPE: PEPTIDE (i x) FEATURE:
        (D) OTHER INFORMATION:

(x i) SEQUENCE DESCRIPTION: SEQ ID NO: 62:

Pro Arg Thr Asn Thr Gly Ser Gly Thr Pro
              5                   10

(2) INFORMATION FOR SEQ ID NO: 63:

(i) SEQUENCE CHARACTERISTICS:
        (A) LENGTH: 9 AMINO ACIDS
        (B) TYPE: AMINO ACID
        (D) TOPOLOGY: LINEAR (i i) MOLECULE TYPE: PEPTIDE (i x) FEATURE:
        (D) OTHER INFORMATION:

(x i) SEQUENCE DESCRIPTION: SEQ ID NO: 63:

Arg Thr Asn Thr Gly Ser Gly Thr Pro
              5

(2) INFORMATION FOR SEQ ID NO: 64:

(i) SEQUENCE CHARACTERISTICS:
        (A) LENGTH: 29 AMINO ACIDS
        (B) TYPE: AMINO ACID
        (D) TOPOLOGY: LINEAR (i i) MOLECULE TYPE: PEPTIDE (i x) FEATURE:
        (D) OTHER INFORMATION:

(x i) SEQUENCE DESCRIPTION: SEQ ID NO: 64:

Ala Thr Gln Arg Leu Ala Asn Phe Leu Val Arg Ser Ser Asn
                  5                   10

Asn Leu Gly Pro Val Leu Pro Pro Thr Asn Val Gly Ser Asn 15                          20                         25

Thr ( 2 ) INFORMATION FOR SEQ ID NO: 65:

( i ) SEQUENCE CHARACTERISTICS:
        ( A ) LENGTH: 28 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 65:

Ala  Thr  Gln  Arg  Leu  Ala  Asn  Phe  Leu  Val  Arg  Ser  Ser  Asn
                    5                        10

Asn  Leu  Gly  Pro  Val  Leu  Pro  Pro  Thr  Asn  Val  Gly  Ser  Asn
15                       20                       25

( 2 ) INFORMATION FOR SEQ ID NO: 66:

( i ) SEQUENCE CHARACTERISTICS:
        ( A ) LENGTH: 27 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 66:

Ala  Thr  Gln  Arg  Leu  Ala  Asn  Phe  Leu  Val  Arg  Ser  Ser  Asn
                    5                        10

Asn  Leu  Gly  Pro  Val  Leu  Pro  Pro  Thr  Asn  Val  Gly  Ser
15                       20                       25

( 2 ) INFORMATION FOR SEQ ID NO: 67:

( i ) SEQUENCE CHARACTERISTICS:
        ( A ) LENGTH: 26 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 67:

Ala  Thr  Gln  Arg  Leu  Ala  Asn  Phe  Leu  Val  Arg  Ser  Ser  Asn
                    5                        10

Asn  Leu  Gly  Pro  Val  Leu  Pro  Pro  Thr  Asn  Val  Gly
15                       20                       25

( 2 ) INFORMATION FOR SEQ ID NO: 68:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 68:

Ala Thr Gln Arg Leu Ala Asn Phe Leu Val Arg Ser Ser Asn
                  5                   10
Asn Leu Gly Pro Val Leu Pro Pro Thr Asn Val
15               20                  25

( 2 ) INFORMATION FOR SEQ ID NO: 69:

( i ) SEQUENCE CHARACTERISTICS:
    ( A ) LENGTH: 24 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 69:

Ala Thr Gln Arg Leu Ala Asn Phe Leu Val Arg Ser Ser Asn
                  5                   10
Asn Leu Gly Pro Val Leu Pro Pro Thr Asn
15               20

( 2 ) INFORMATION FOR SEQ ID NO: 70:

( i ) SEQUENCE CHARACTERISTICS:
    ( A ) LENGTH: 23 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 70:

Ala Thr Gln Arg Leu Ala Asn Phe Leu Val Arg Ser Ser Asn
                  5                   10
Asn Leu Gly Pro Val Leu Pro Pro Thr
15               20

( 2 ) INFORMATION FOR SEQ ID NO: 71:

( i ) SEQUENCE CHARACTERISTICS:
    ( A ) LENGTH: 22 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 71:

Ala Thr Gln Arg Leu Ala Asn Phe Leu Val Arg Ser Ser Asn
                  5                   10
Asn Leu Gly Pro Val Leu Pro Pro
15               20

( 2 ) INFORMATION FOR SEQ ID NO: 72:

( i ) SEQUENCE CHARACTERISTICS:
    ( A ) LENGTH: 29 AMINO ACIDS
    ( B ) TYPE: AMINO ACID
    ( D ) TOPOLOGY: LINEAR ( i i ) MOLECULE TYPE: PEPTIDE (ix) FEATURE:
    (D) OTHER INFORMATION:

(xi) SEQUENCE DESCRIPTION: SEQ ID NO: 72:

Val Thr His Arg Leu Ala Gly Leu Leu Ser Arg Ser Gly Gly
              5                       10
Val Val Lys Asn Asn Phe Val Pro Thr Asn Val Gly Ser Lys
15                  20                  25
Ala (2) INFORMATION FOR SEQ ID NO: 73:

(i) SEQUENCE CHARACTERISTICS:
        (A) LENGTH: 28 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 73:

Val Thr His Arg Leu Ala Gly Leu Leu Ser Arg Ser Gly Gly
              5                       10
Val Val Lys Asn Asn Phe Val Pro Thr Asn Val Gly Ser Lys
15                  20                  25

(2) INFORMATION FOR SEQ ID NO: 74:

(i) SEQUENCE CHARACTERISTICS:
        (A) LENGTH: 27 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 74:

Val Thr His Arg Leu Ala Gly Leu Leu Ser Arg Ser Gly Gly
              5                       10
Val Val Lys Asn Asn Phe Val Pro Thr Asn Val Gly Ser
15                  20                  25

(2) INFORMATION FOR SEQ ID NO: 75:

(i) SEQUENCE CHARACTERISTICS:
        (A) LENGTH: 26 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 75:

Val Thr His Arg Leu Ala Gly Leu Leu Ser Arg Ser Gly Gly
              5                       10
Val Val Lys Asn Asn Phe Val Pro Thr Asn Val Gly
15                  20                  25

(2) INFORMATION FOR SEQ ID NO: 76:

( i ) SEQUENCE CHARACTERISTICS:
    ( A ) LENGTH: 25 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 76:

Val Thr His Arg Leu Ala Gly Leu Leu Ser Arg Ser Gly Gly
                5                   10
Val Val Lys Asn Asn Phe Val Pro Thr Asn Val
15              20                  25

( 2 ) INFORMATION FOR SEQ ID NO: 77:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 77:

Val Thr His Arg Leu Ala Gly Leu Leu Ser Arg Ser Gly Gly
                5                   10
Val Val Lys Asn Asn Phe Val Pro Thr Asn
15              20

( 2 ) INFORMATION FOR SEQ ID NO: 78:

( i ) SEQUENCE CHARACTERISTICS:
        ( A ) LENGTH: 23 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 78:

Val Thr His Arg Leu Ala Gly Leu Leu Ser Arg Ser Gly Gly
                5                   10
Val Val Lys Asn Asn Phe Val Pro Thr
15              20

( 2 ) INFORMATION FOR SEQ ID NO: 79:

( i ) SEQUENCE CHARACTERISTICS:
        ( A ) LENGTH: 22 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 79:

Val Thr His Arg Leu Ala Gly Leu Leu Ser Arg Ser Gly Gly
                5                   10
Val Val Lys Asn Asn Phe Val Pro
15              20

( 2 ) INFORMATION FOR SEQ ID NO: 80:

( i ) SEQUENCE CHARACTERISTICS:
( A ) LENGTH: 24 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 80:

Val Leu Gly Lys Leu Ser Gln Glu Leu His Lys Leu Gln Thr
                 5                           10
Tyr Pro Arg Thr Asn Thr Gly Ser Gly Thr
 15                   20

( 2 ) INFORMATION FOR SEQ ID NO: 81:

( i ) SEQUENCE CHARACTERISTICS:
( A ) LENGTH: 23 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 81:

Val Leu Gly Lys Leu Ser Gln Glu Leu His Lys Leu Gln Thr
                 5                           10
Tyr Pro Arg Thr Asn Thr Gly Ser Gly
 15                   20

( 2 ) INFORMATION FOR SEQ ID NO: 82:

( i ) SEQUENCE CHARACTERISTICS:
( A ) LENGTH: 22 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 82:

Val Leu Gly Lys Leu Ser Gln Glu Leu His Lys Leu Gln Thr
                 5                           10
Tyr Pro Arg Thr Asn Thr Gly Ser
 15                   20

( 2 ) INFORMATION FOR SEQ ID NO: 83:

( i ) SEQUENCE CHARACTERISTICS:
( A ) LENGTH: 21 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 83:

Val Leu Gly Lys Leu Ser Gln Glu Leu His Lys Leu Gln Thr

```
                            5                           10
Tyr  Pro  Arg  Thr  Asn  Thr  Gly
15                      20
```

( 2 ) INFORMATION FOR SEQ ID NO: 84:

( i ) SEQUENCE CHARACTERISTICS:
        ( A ) LENGTH: 20 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 84:

```
Val  Leu  Gly  Lys  Leu  Ser  Gln  Glu  Leu  His  Lys  Leu  Gln  Thr
                    5                        10
Tyr  Pro  Arg  Thr  Asn  Thr
15                      20
```

( 2 ) INFORMATION FOR SEQ ID NO: 85:

( i ) SEQUENCE CHARACTERISTICS:
        ( A ) LENGTH: 19 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 85:

```
Val  Leu  Gly  Lys  Leu  Ser  Gln  Glu  Leu  His  Lys  Leu  Gln  Thr
                    5                        10
Tyr  Pro  Arg  Thr  Asn
15
```

( 2 ) INFORMATION FOR SEQ ID NO: 86:

( i ) SEQUENCE CHARACTERISTICS:
        ( A ) LENGTH: 18 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 86:

```
Val  Leu  Gly  Lys  Leu  Ser  Gln  Glu  Leu  His  Lys  Leu  Gln  Thr
                    5                        10
Tyr  Pro  Arg  Thr
15
```

( 2 ) INFORMATION FOR SEQ ID NO: 87:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 87:

Val  Leu  Gly  Lys  Leu  Ser  Gln  Glu  Leu  His  Lys  Leu  Gln  Thr
                    5                        10

Tyr  Pro  Arg
15

( 2 ) INFORMATION FOR SEQ ID NO: 88:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 88:

Val  Leu  Gly  Lys  Leu  Ser  Gln  Glu  Leu  His  Lys  Leu  Gln  Thr
                    5                        10

Tyr  Pro
15

( 2 ) INFORMATION FOR SEQ ID NO: 89:

( i ) SEQUENCE CHARACTERISTICS:
        ( A ) LENGTH: 15 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 89:

Val  Leu  Gly  Lys  Leu  Ser  Gln  Glu  Leu  His  Lys  Leu  Gln  Thr
                    5                        10

Tyr
15

( 2 ) INFORMATION FOR SEQ ID NO: 90:

( i ) SEQUENCE CHARACTERISTICS:
        ( A ) LENGTH: 29 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 90:

Ala  Thr  Gln  Arg  Leu  Ala  Asn  Phe  Leu  Val  Arg  Ser  Asn  Asn
                    5                        10

Leu  Gly  Pro  Val  Leu  Pro  Pro  Thr  Asn  Val  Gly  Ser  Asn  Thr
15                       20                       25

Tyr ( 2 ) INFORMATION FOR SEQ ID NO: 91:

( i ) SEQUENCE CHARACTERISTICS:
        ( A ) LENGTH: 29 AMINO ACIDS
        ( B ) TYPE: AMINO ACID (D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 91:

Ala Thr Gln Arg Leu Ala Asn Phe Leu Val Arg Ser Ser Asn
                 5                   10
Asn Leu Gly Pro Val Leu Pro Thr Asn Val Gly Ser Asn Thr
15               20                  25
Tyr (2) INFORMATION FOR SEQ ID NO: 92:

(i) SEQUENCE CHARACTERISTICS:
(A) LENGTH: 20 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 92:

Ala Thr Gln Arg Leu Ala Asn Phe Leu Val Arg Ser Thr Asn
                 5                   10
Val Gly Ser Asn Thr Tyr
15                  20

(2) INFORMATION FOR SEQ ID NO: 93:

(i) SEQUENCE CHARACTERISTICS:
(A) LENGTH: 24 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 93:

Ala Thr Gln Arg Leu Ala Asn Phe Leu Val Arg Ser Ser Asn
                 5                   10
Asn Leu Thr Asn Val Gly Ser Asn Thr Tyr
15               20

(2) INFORMATION FOR SEQ ID NO: 94:

(i) SEQUENCE CHARACTERISTICS:
(A) LENGTH: 29 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 94:

Val Thr His Arg Leu Ala Gly Leu Leu Ser Arg Gly Gly Val
                 5                   10
Val Lys Asn Asn Phe Val Pro Thr Asn Val Gly Ser Lys Ala
15               20                  25

Phe ( 2 ) INFORMATION FOR SEQ ID NO: 95:

( i ) SEQUENCE CHARACTERISTICS:
        ( A ) LENGTH: 19 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 95:

Val Thr His Arg Leu Ala Gly Leu Leu Ser Arg Thr Asn Val
            5                        10

Gly Ser Lys Ala Phe
15

( 2 ) INFORMATION FOR SEQ ID NO: 96:

( i ) SEQUENCE CHARACTERISTICS:
        ( A ) LENGTH: 29 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 96:

Val Thr His Arg Leu Ala Gly Leu Leu Ser Arg Ser Gly Gly
            5                        10

Val Val Lys Asn Asn Phe Val Thr Asn Val Gly Ser Lys Ala
15                20                          25

Phe ( 2 ) INFORMATION FOR SEQ ID NO: 97:

( i ) SEQUENCE CHARACTERISTICS:
        ( A ) LENGTH: 20 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 97:

Val Thr His Arg Leu Ala Gly Leu Leu Ser Arg Ser Thr Asn
            5                        10

Val Gly Ser Lys Ala Phe
15                20

( 2 ) INFORMATION FOR SEQ ID NO: 98:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 98:

Val Leu Gly Lys Leu Ser Gln Glu Leu His Lys Leu Gln Thr
                  5                     10
Tyr Pro Thr Asn Thr Gly Ser Gly Thr Pro
15                   20

( 2 ) INFORMATION FOR SEQ ID NO: 99:

( i ) SEQUENCE CHARACTERISTICS:
        ( A ) LENGTH: 19 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 99:

Val Leu Gly Lys Leu Ser Gln Glu Leu His Lys Thr Asn Thr
                  5                     10
Gly Ser Gly Thr Pro
15

( 2 ) INFORMATION FOR SEQ ID NO: 100:

( i ) SEQUENCE CHARACTERISTICS:
        ( A ) LENGTH: 14 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 100:

Val Leu Gly Lys Leu Ser Gln Glu Leu His Lys Gly Thr Pro
                  5                     10

( 2 ) INFORMATION FOR SEQ ID NO: 101:

( i ) SEQUENCE CHARACTERISTICS:
        ( A ) LENGTH: 20 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 101:

Val Leu Gly Lys Leu Ser Gln Glu Leu His Lys Arg Thr Asn
                  5                     10
Thr Gly Ser Gly Thr Pro
15                  20

( 2 ) INFORMATION FOR SEQ ID NO: 102:

( i ) SEQUENCE CHARACTERISTICS:
        ( A ) LENGTH: 21 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 102:

Leu Gly Lys Leu Ser Gln Glu Leu His Lys Leu Pro Arg Thr
                  5                   10
Asn Thr Gly Ser Gly Thr Pro
15                  20

( 2 ) INFORMATION FOR SEQ ID NO: 103:

( i ) SEQUENCE CHARACTERISTICS:
          ( A ) LENGTH: 28 AMINO ACIDS
          ( B ) TYPE: AMINO ACID
          ( D ) TOPOLOGY: LINEAR ( i i ) MOLECULE TYPE: PEPTIDE ( i x ) FEATURE:
          ( D ) OTHER INFORMATION:

( x i ) SEQUENCE DESCRIPTION: SEQ ID NO: 103:

Thr Gln Arg Leu Ala Asn Phe Leu Val Arg Ser Ser Asn Asn
                  5                   10
Leu Gly Pro Val Leu Pro Pro Thr Asn Val Gly Ser Asn Thr
15                  20                  25

( 2 ) INFORMATION FOR SEQ ID NO: 104:

( i ) SEQUENCE CHARACTERISTICS:
          ( A ) LENGTH: 27 AMINO ACIDS
          ( B ) TYPE: AMINO ACID
          ( D ) TOPOLOGY: LINEAR ( i i ) MOLECULE TYPE: PEPTIDE ( i x ) FEATURE:
          ( D ) OTHER INFORMATION:

( x i ) SEQUENCE DESCRIPTION: SEQ ID NO: 104:

Thr Gln Arg Leu Ala Asn Phe Leu Val Arg Ser Ser Asn Asn
                  5                   10
Leu Gly Pro Val Leu Pro Pro Thr Asn Val Gly Ser Asn
15                  20                  25

( 2 ) INFORMATION FOR SEQ ID NO: 105:

( i ) SEQUENCE CHARACTERISTICS:
          ( A ) LENGTH: 26 AMINO ACIDS
          ( B ) TYPE: AMINO ACID
          ( D ) TOPOLOGY: LINEAR ( i i ) MOLECULE TYPE: PEPTIDE ( i x ) FEATURE:
          ( D ) OTHER INFORMATION:

( x i ) SEQUENCE DESCRIPTION: SEQ ID NO: 105:

Thr Gln Arg Leu Ala Asn Phe Leu Val Arg Ser Ser Asn Asn
                  5                   10
Leu Gly Pro Val Leu Pro Pro Thr Asn Val Gly Ser
15                  20                  25

( 2 ) INFORMATION FOR SEQ ID NO: 106:

( i ) SEQUENCE CHARACTERISTICS:
          ( A ) LENGTH: 25 AMINO ACIDS
          ( B ) TYPE: AMINO ACID
          ( D ) TOPOLOGY: LINEAR (ii) MOLECULE TYPE: PEPTIDE (ix) FEATURE:
    (D) OTHER INFORMATION:

(xi) SEQUENCE DESCRIPTION: SEQ ID NO: 106:

Thr Gln Arg Leu Ala Asn Phe Leu Val Arg Ser Ser Asn Asn
                 5                    10

Leu Gly Pro Val Leu Pro Pro Thr Asn Val Gly
15                  20                    25

(2) INFORMATION FOR SEQ ID NO: 107:

(i) SEQUENCE CHARACTERISTICS:
        (A) LENGTH: 24 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 107:

Thr Gln Arg Leu Ala Asn Phe Leu Val Arg Ser Ser Asn Asn
                 5                    10

Leu Gly Pro Val Leu Pro Pro Thr Asn Val
15                  20

(2) INFORMATION FOR SEQ ID NO: 108:

(i) SEQUENCE CHARACTERISTICS:
        (A) LENGTH: 23 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 108:

Thr Gln Arg Leu Ala Asn Phe Leu Val Arg Ser Ser Asn Asn
                 5                    10

Leu Gly Pro Val Leu Pro Pro Thr Asn
15                  20

(2) INFORMATION FOR SEQ ID NO: 109:

(i) SEQUENCE CHARACTERISTICS:
        (A) LENGTH: 22 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 109:

Thr Gln Arg Leu Ala Asn Phe Leu Val Arg Ser Ser Asn Asn
                 5                    10

Leu Gly Pro Val Leu Pro Pro Thr
15                  20

(2) INFORMATION FOR SEQ ID NO: 110:

(i) SEQUENCE CHARACTERISTICS:

(A) LENGTH: 21 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 110:

Thr Gln Arg Leu Ala Asn Phe Leu Val Arg Ser Ser Asn Asn
                    5                   10

Leu Gly Pro Val Leu Pro Pro
15                  20

(2) INFORMATION FOR SEQ ID NO: 111:

(i) SEQUENCE CHARACTERISTICS:
(A) LENGTH: 27 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 111:

Gln Arg Leu Ala Asn Phe Leu Val Arg Ser Ser Asn Asn Leu
                5                   10

Gly Pro Val Leu Pro Pro Thr Asn Val Gly Ser Asn Thr
15                  20                  25

(2) INFORMATION FOR SEQ ID NO: 112:

(i) SEQUENCE CHARACTERISTICS:
(A) LENGTH: 26 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 112:

Gln Arg Leu Ala Asn Phe Leu Val Arg Ser Ser Asn Asn Leu
                5                   10

Gly Pro Val Leu Pro Pro Thr Asn Val Gly Ser Asn
15                  20                  25

(2) INFORMATION FOR SEQ ID NO: 113:

(i) SEQUENCE CHARACTERISTICS:
(A) LENGTH: 25 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 113:

Gln Arg Leu Ala Asn Phe Leu Val Arg Ser Ser Asn Asn Leu
                5                   10

Gly Pro Val Leu Pro Pro Thr Asn Val Gly Ser
15                  20                  25

( 2 ) INFORMATION FOR SEQ ID NO: 114:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 114:

Gln Arg Leu Ala Asn Phe Leu Val Arg Ser Ser Asn Asn Leu
                5                        10

Gly Pro Val Leu Pro Pro Thr Asn Val Gly
15                20

( 2 ) INFORMATION FOR SEQ ID NO: 115:

( i ) SEQUENCE CHARACTERISTICS:
        ( A ) LENGTH: 23 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 115:

Gln Arg Leu Ala Asn Phe Leu Val Arg Ser Ser Asn Asn Leu
                5                        10

Gly Pro Val Leu Pro Pro Thr Asn Val
15                20

( 2 ) INFORMATION FOR SEQ ID NO: 116:

( i ) SEQUENCE CHARACTERISTICS:
        ( A ) LENGTH: 22 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 116:

Gln Arg Leu Ala Asn Phe Leu Val Arg Ser Ser Asn Asn Leu
                5                        10

Gly Pro Val Leu Pro Pro Thr Asn
15                20

( 2 ) INFORMATION FOR SEQ ID NO: 117:

( i ) SEQUENCE CHARACTERISTICS:
        ( A ) LENGTH: 21 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 117:

Gln Arg Leu Ala Asn Phe Leu Val Arg Ser Ser Asn Asn Leu
                5                        10

```
Gly Pro Val Leu Pro Pro Thr
15                  20
```

( 2 ) INFORMATION FOR SEQ ID NO: 118:

( i ) SEQUENCE CHARACTERISTICS:
        ( A ) LENGTH: 20 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 118:

```
Gln Arg Leu Ala Asn Phe Leu Val Arg Ser Ser Asn Asn Leu
                5                       10
Gly Pro Val Leu Pro Pro
15                  20
```

( 2 ) INFORMATION FOR SEQ ID NO: 119:

( i ) SEQUENCE CHARACTERISTICS:
        ( A ) LENGTH: 26 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 119:

```
Arg Leu Ala Asn Phe Leu Val Arg Ser Ser Asn Asn Leu Gly
                5                       10
Pro Val Leu Pro Pro Thr Asn Val Gly Ser Asn Thr
15                  20                  25
```

( 2 ) INFORMATION FOR SEQ ID NO: 120:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 120:

```
Arg Leu Ala Asn Phe Leu Val Arg Ser Ser Asn Asn Leu Gly
                5                       10
Pro Val Leu Pro Pro Thr Asn Val Gly Ser Asn
15                  20                  25
```

( 2 ) INFORMATION FOR SEQ ID NO: 121:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 121:

Arg Leu Ala Asn Phe Leu Val Arg Ser Ser Asn Asn Leu Gly
                  5                   10

Pro Val Leu Pro Pro Thr Asn Val Gly Ser
15                  20

( 2 ) INFORMATION FOR SEQ ID NO: 122:

( i ) SEQUENCE CHARACTERISTICS:
        ( A ) LENGTH: 23 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 122:

Arg Leu Ala Asn Phe Leu Val Arg Ser Ser Asn Asn Leu Gly
                  5                   10

Pro Val Leu Pro Pro Thr Asn Val Gly
15                  20

( 2 ) INFORMATION FOR SEQ ID NO: 123:

( i ) SEQUENCE CHARACTERISTICS:
        ( A ) LENGTH: 22 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 123:

Arg Leu Ala Asn Phe Leu Val Arg Ser Ser Asn Asn Leu Gly
                  5                   10

Pro Val Leu Pro Pro Thr Asn Val
15                  20

( 2 ) INFORMATION FOR SEQ ID NO: 124:

( i ) SEQUENCE CHARACTERISTICS:
        ( A ) LENGTH: 21 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 124:

Arg Leu Ala Asn Phe Leu Val Arg Ser Ser Asn Asn Leu Gly
                  5                   10

Pro Val Leu Pro Pro Thr Asn
15                  20

( 2 ) INFORMATION FOR SEQ ID NO: 125:

( i ) SEQUENCE CHARACTERISTICS:
        ( A ) LENGTH: 20 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 125:

Arg Leu Ala Asn Phe Leu Val Arg Ser Ser Asn Asn Leu Gly
                 5                   10
Pro Val Leu Pro Pro Thr
15              20

( 2 ) INFORMATION FOR SEQ ID NO: 126:

( i ) SEQUENCE CHARACTERISTICS:
            ( A ) LENGTH: 19 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 126:

Arg Leu Ala Asn Phe Leu Val Arg Ser Ser Asn Asn Leu Gly
                 5                   10
Pro Val Leu Pro Pro
15

( 2 ) INFORMATION FOR SEQ ID NO: 127:

( i ) SEQUENCE CHARACTERISTICS:
            ( A ) LENGTH: 28 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 127:

Thr His Arg Leu Ala Gly Leu Leu Ser Arg Ser Gly Gly Val
                 5                   10
Val Lys Asn Asn Phe Val Pro Thr Asn Val Gly Ser Lys Ala
15              20                  25

( 2 ) INFORMATION FOR SEQ ID NO: 128:

( i ) SEQUENCE CHARACTERISTICS:
            ( A ) LENGTH: 27 AMINO ACIDS
            ( B ) TYPE: AMINO ACID
            ( D ) TOPOLOGY: LINEAR ( i i ) MOLECULE TYPE: PEPTIDE ( i x ) FEATURE:
            ( D ) OTHER INFORMATION:

( x i ) SEQUENCE DESCRIPTION: SEQ ID NO: 128:

Thr His Arg Leu Ala Gly Leu Leu Ser Arg Ser Gly Gly Val
                 5                   10
Val Lys Asn Asn Phe Val Pro Thr Asn Val Gly Ser Lys
15              20                  25

( 2 ) INFORMATION FOR SEQ ID NO: 129:

( i ) SEQUENCE CHARACTERISTICS:
            ( A ) LENGTH: 26 AMINO ACIDS (B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 129:

Thr His Arg Leu Ala Gly Leu Leu Ser Arg Ser Gly Gly Val
              5                   10
Val Lys Asn Asn Phe Val Pro Thr Asn Val Gly Ser
15                  20                  25

(2) INFORMATION FOR SEQ ID NO: 130:

(i) SEQUENCE CHARACTERISTICS:
(A) LENGTH: 25 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 130:

Thr His Arg Leu Ala Gly Leu Leu Ser Arg Ser Gly Gly Val
              5                   10
Val Lys Asn Asn Phe Val Pro Thr Asn Val Gly
15                  20                  25

(2) INFORMATION FOR SEQ ID NO: 131:

(i) SEQUENCE CHARACTERISTICS:
(A) LENGTH: 24 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 131:

Thr His Arg Leu Ala Gly Leu Leu Ser Arg Ser Gly Gly Val
              5                   10
Val Lys Asn Asn Phe Val Pro Thr Asn Val
15                  20

(2) INFORMATION FOR SEQ ID NO: 132:

(i) SEQUENCE CHARACTERISTICS:
(A) LENGTH: 23 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 132:

Thr His Arg Leu Ala Gly Leu Leu Ser Arg Ser Gly Gly Val
              5                   10
Val Lys Asn Asn Phe Val Pro Thr Asn
15                  20

( 2 ) INFORMATION FOR SEQ ID NO: 133:

( i ) SEQUENCE CHARACTERISTICS:
       ( A ) LENGTH: 22 AMINO ACIDS
       ( B ) TYPE: AMINO ACID
       ( D ) TOPOLOGY: LINEAR ( i i ) MOLECULE TYPE: PEPTIDE ( i x ) FEATURE:
       ( D ) OTHER INFORMATION:

( x i ) SEQUENCE DESCRIPTION: SEQ ID NO: 133:

Thr His Arg Leu Ala Gly Leu Leu Ser Arg Ser Gly Gly Val
                    5                           10
Val Lys Asn Asn Phe Val Pro Thr
15                  20

( 2 ) INFORMATION FOR SEQ ID NO: 134:

( i ) SEQUENCE CHARACTERISTICS:
       ( A ) LENGTH: 21 AMINO ACIDS
       ( B ) TYPE: AMINO ACID
       ( D ) TOPOLOGY: LINEAR ( i i ) MOLECULE TYPE: PEPTIDE ( i x ) FEATURE:
       ( D ) OTHER INFORMATION:

( x i ) SEQUENCE DESCRIPTION: SEQ ID NO: 134:

Thr His Arg Leu Ala Gly Leu Leu Ser Arg Ser Gly Gly Val
                    5                           10
Val Lys Asn Asn Phe Val Pro
15                  20

( 2 ) INFORMATION FOR SEQ ID NO: 135:

( i ) SEQUENCE CHARACTERISTICS:
       ( A ) LENGTH: 27 AMINO ACIDS
       ( B ) TYPE: AMINO ACID
       ( D ) TOPOLOGY: LINEAR ( i i ) MOLECULE TYPE: PEPTIDE ( i x ) FEATURE:
       ( D ) OTHER INFORMATION:

( x i ) SEQUENCE DESCRIPTION: SEQ ID NO: 135:

His Arg Leu Ala Gly Leu Leu Ser Arg Ser Gly Gly Val Val
                5                           10
Lys Asn Asn Phe Val Pro Thr Asn Val Gly Ser Lys Ala
15              20                      25

( 2 ) INFORMATION FOR SEQ ID NO: 136:

( i ) SEQUENCE CHARACTERISTICS:
       ( A ) LENGTH: 26 AMINO ACIDS
       ( B ) TYPE: AMINO ACID
       ( D ) TOPOLOGY: LINEAR ( i i ) MOLECULE TYPE: PEPTIDE ( i x ) FEATURE:
       ( D ) OTHER INFORMATION:

( x i ) SEQUENCE DESCRIPTION: SEQ ID NO: 136:

His Arg Leu Ala Gly Leu Leu Ser Arg Ser Gly Gly Val Val
                5                           10

```
Lys  Asn  Asn  Phe  Val  Pro  Thr  Asn  Val  Gly  Ser  Lys
 15                  20                       25
```

(2) INFORMATION FOR SEQ ID NO: 137:

(i) SEQUENCE CHARACTERISTICS:
        (A) LENGTH: 25 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 137:

```
His  Arg  Leu  Ala  Gly  Leu  Leu  Ser  Arg  Ser  Gly  Gly  Val  Val
               5                             10

Lys  Asn  Asn  Phe  Val  Pro  Thr  Asn  Val  Gly  Ser
 15                  20                       25
```

(2) INFORMATION FOR SEQ ID NO: 138:

(i) SEQUENCE CHARACTERISTICS:
        (A) LENGTH: 24 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 138:

```
His  Arg  Leu  Ala  Gly  Leu  Leu  Ser  Arg  Ser  Gly  Gly  Val  Val
               5                             10

Lys  Asn  Asn  Phe  Val  Pro  Thr  Asn  Val  Gly
 15                  20
```

(2) INFORMATION FOR SEQ ID NO: 139:

(i) SEQUENCE CHARACTERISTICS:
        (A) LENGTH: 23 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 139:

```
His  Arg  Leu  Ala  Gly  Leu  Leu  Ser  Arg  Ser  Gly  Gly  Val  Val
               5                             10

Lys  Asn  Asn  Phe  Val  Pro  Thr  Asn  Val
 15                  20
```

(2) INFORMATION FOR SEQ ID NO: 140:

(i) SEQUENCE CHARACTERISTICS:
        (A) LENGTH: 22 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 140:

His Arg Leu Ala Gly Leu Leu Ser Arg Ser Gly Gly Val Val
              5                           10

Lys Asn Asn Phe Val Pro Thr Asn
 15                  20

( 2 ) INFORMATION FOR SEQ ID NO: 141:

( i ) SEQUENCE CHARACTERISTICS:
                  ( A ) LENGTH: 21 AMINO ACIDS
                  ( B ) TYPE: AMINO ACID
                  ( D ) TOPOLOGY: LINEAR ( i i ) MOLECULE TYPE: PEPTIDE ( i x ) FEATURE:
                  ( D ) OTHER INFORMATION:

( x i ) SEQUENCE DESCRIPTION: SEQ ID NO: 141:

His Arg Leu Ala Gly Leu Leu Ser Arg Ser Gly Gly Val Val
              5                           10

Lys Asn Asn Phe Val Pro Thr
 15                  20

( 2 ) INFORMATION FOR SEQ ID NO: 142:

( i ) SEQUENCE CHARACTERISTICS:
                  ( A ) LENGTH: 20 AMINO ACIDS
                  ( B ) TYPE: AMINO ACID
                  ( D ) TOPOLOGY: LINEAR ( i i ) MOLECULE TYPE: PEPTIDE ( i x ) FEATURE:
                  ( D ) OTHER INFORMATION:

( x i ) SEQUENCE DESCRIPTION: SEQ ID NO: 142:

His Arg Leu Ala Gly Leu Leu Ser Arg Ser Gly Gly Val Val
              5                           10

Lys Asn Asn Phe Val Pro
 15                  20

( 2 ) INFORMATION FOR SEQ ID NO: 143:

( i ) SEQUENCE CHARACTERISTICS:
                  ( A ) LENGTH: 26 AMINO ACIDS
                  ( B ) TYPE: AMINO ACID
                  ( D ) TOPOLOGY: LINEAR ( i i ) MOLECULE TYPE: PEPTIDE ( i x ) FEATURE:
                  ( D ) OTHER INFORMATION:

( x i ) SEQUENCE DESCRIPTION: SEQ ID NO: 143:

Arg Leu Ala Gly Leu Leu Ser Arg Ser Gly Gly Val Val Lys
              5                           10

Asn Asn Phe Val Pro Thr Asn Val Gly Ser Lys Ala
 15                  20                  25

( 2 ) INFORMATION FOR SEQ ID NO: 144:

( i ) SEQUENCE CHARACTERISTICS:
                  ( A ) LENGTH: 25 AMINO ACIDS
                  ( B ) TYPE: AMINO ACID
                  ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 144:

Arg Leu Ala Gly Leu Leu Ser Arg Ser Gly Gly Val Val Lys
                  5                   10

Asn Asn Phe Val Pro Thr Asn Val Gly Ser Lys
15                  20                  25

( 2 ) INFORMATION FOR SEQ ID NO: 145:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 145:

Arg Leu Ala Gly Leu Leu Ser Arg Ser Gly Gly Val Val Lys
                  5                   10

Asn Asn Phe Val Pro Thr Asn Val Gly Ser
15                  20

( 2 ) INFORMATION FOR SEQ ID NO: 146:

( i ) SEQUENCE CHARACTERISTICS:
        ( A ) LENGTH: 23 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 146:

Arg Leu Ala Gly Leu Leu Ser Arg Ser Gly Gly Val Val Lys
                  5                   10

Asn Asn Phe Val Pro Thr Asn Val Gly
15                  20

( 2 ) INFORMATION FOR SEQ ID NO: 147:

( i ) SEQUENCE CHARACTERISTICS:
        ( A ) LENGTH: 22 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 147:

Arg Leu Ala Gly Leu Leu Ser Arg Ser Gly Gly Val Val Lys
                  5                   10

Asn Asn Phe Val Pro Thr Asn Val
15                  20

( 2 ) INFORMATION FOR SEQ ID NO: 148:

( i ) SEQUENCE CHARACTERISTICS:
        ( A ) LENGTH: 21 AMINO ACIDS
        ( B ) TYPE: AMINO ACID ( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 148:

Arg Leu Ala Gly Leu Leu Ser Arg Ser Gly Gly Val Val Lys
                  5                   10
Asn Asn Phe Val Pro Thr Asn
15                  20

( 2 ) INFORMATION FOR SEQ ID NO: 149:

( i ) SEQUENCE CHARACTERISTICS:
( A ) LENGTH: 20 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 149:

Arg Leu Ala Gly Leu Leu Ser Arg Ser Gly Gly Val Val Lys
                  5                   10
Asn Asn Phe Val Pro Thr
15                  20

( 2 ) INFORMATION FOR SEQ ID NO: 150:

( i ) SEQUENCE CHARACTERISTICS:
( A ) LENGTH: 19 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 150:

Arg Leu Ala Gly Leu Leu Ser Arg Ser Gly Gly Val Val Lys
                  5                   10
Asn Asn Phe Val Pro
15

( 2 ) INFORMATION FOR SEQ ID NO: 151:

( i ) SEQUENCE CHARACTERISTICS:
( A ) LENGTH: 23 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 151:

Leu Gly Lys Leu Ser Gln Glu Leu His Lys Leu Gln Thr Tyr
                  5                   10
Pro Arg Thr Asn Thr Gly Ser Gly Thr
15                  20

( 2 ) INFORMATION FOR SEQ ID NO: 152:

(i) SEQUENCE CHARACTERISTICS:
  (A) LENGTH: 22 AMINO ACIDS
  (B) TYPE: AMINO ACID
  (D) TOPOLOGY: LINEAR (ii) MOLECULE TYPE: PEPTIDE (ix) FEATURE:
  (D) OTHER INFORMATION:

(xi) SEQUENCE DESCRIPTION: SEQ ID NO: 152:

Leu Gly Lys Leu Ser Gln Glu Leu His Lys Leu Gln Thr Tyr
                  5                   10
Pro Arg Thr Asn Thr Gly Ser Gly
15                  20

(2) INFORMATION FOR SEQ ID NO: 153:

(i) SEQUENCE CHARACTERISTICS:
  (A) LENGTH: 21 AMINO ACIDS
  (B) TYPE: AMINO ACID
  (D) TOPOLOGY: LINEAR (ii) MOLECULE TYPE: PEPTIDE (ix) FEATURE:
  (D) OTHER INFORMATION:

(xi) SEQUENCE DESCRIPTION: SEQ ID NO: 153:

Leu Gly Lys Leu Ser Gln Glu Leu His Lys Leu Gln Thr Tyr
                  5                   10
Pro Arg Thr Asn Thr Gly Ser
15                  20

(2) INFORMATION FOR SEQ ID NO: 154:

(i) SEQUENCE CHARACTERISTICS:
  (A) LENGTH: 20 AMINO ACIDS
  (B) TYPE: AMINO ACID
  (D) TOPOLOGY: LINEAR (ii) MOLECULE TYPE: PEPTIDE (ix) FEATURE:
  (D) OTHER INFORMATION:

(xi) SEQUENCE DESCRIPTION: SEQ ID NO: 154:

Leu Gly Lys Leu Ser Gln Glu Leu His Lys Leu Gln Thr Tyr
                  5                   10
Pro Arg Thr Asn Thr Gly
15                  20

(2) INFORMATION FOR SEQ ID NO: 155:

(i) SEQUENCE CHARACTERISTICS:
  (A) LENGTH: 19 AMINO ACIDS
  (B) TYPE: AMINO ACID
  (D) TOPOLOGY: LINEAR (ii) MOLECULE TYPE: PEPTIDE (ix) FEATURE:
  (D) OTHER INFORMATION:

(xi) SEQUENCE DESCRIPTION: SEQ ID NO: 155:

Leu Gly Lys Leu Ser Gln Glu Leu His Lys Leu Gln Thr Tyr
                  5                   10
Pro Arg Thr Asn Thr

15

(2) INFORMATION FOR SEQ ID NO: 156:

(i) SEQUENCE CHARACTERISTICS:
        (A) LENGTH: 18 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 156:

Leu Gly Lys Leu Ser Gln Glu Leu His Lys Leu Gln Thr Tyr
            5                      10

Pro Arg Thr Asn
15

(2) INFORMATION FOR SEQ ID NO: 157:

(i) SEQUENCE CHARACTERISTICS:
        (A) LENGTH: 17 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 157:

Leu Gly Lys Leu Ser Gln Glu Leu His Lys Leu Gln Thr Tyr
            5                      10

Pro Arg Thr
15

(2) INFORMATION FOR SEQ ID NO: 158:

(i) SEQUENCE CHARACTERISTICS:
        (A) LENGTH: 16 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 158:

Leu Gly Lys Leu Ser Gln Glu Leu His Lys Leu Gln Thr Tyr
            5                      10

Pro Arg
15

(2) INFORMATION FOR SEQ ID NO: 159:

(i) SEQUENCE CHARACTERISTICS:
        (A) LENGTH: 22 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 159:

```
Gly Lys Leu Ser Gln Glu Leu His Lys Leu Gln Thr Tyr Pro
                  5                   10
Arg Thr Asn Thr Gly Ser Gly Thr
 15                  20
```

( 2 ) INFORMATION FOR SEQ ID NO: 160:

( i ) SEQUENCE CHARACTERISTICS:
        ( A ) LENGTH: 21 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 160:

```
Gly Lys Leu Ser Gln Glu Leu His Lys Leu Gln Thr Tyr Pro
                  5                   10
Arg Thr Asn Thr Gly Ser Gly
 15                  20
```

( 2 ) INFORMATION FOR SEQ ID NO: 161:

( i ) SEQUENCE CHARACTERISTICS:
        ( A ) LENGTH: 20 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 161:

```
Gly Lys Leu Ser Gln Glu Leu His Lys Leu Gln Thr Tyr Pro
                  5                   10
Arg Thr Asn Thr Gly Ser
 15                  20
```

( 2 ) INFORMATION FOR SEQ ID NO: 162:

( i ) SEQUENCE CHARACTERISTICS:
        ( A ) LENGTH: 19 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 162:

```
Gly Lys Leu Ser Gln Glu Leu His Lys Leu Gln Thr Tyr Pro
                  5                   10
Arg Thr Asn Thr Gly
 15
```

( 2 ) INFORMATION FOR SEQ ID NO: 163:

( i ) SEQUENCE CHARACTERISTICS:
        ( A ) LENGTH: 18 AMINO ACIDS
        ( B ) TYPE: AMINO ACID
        ( D ) TOPOLOGY: LINEAR ( i i ) MOLECULE TYPE: PEPTIDE ( i x ) FEATURE:

(D) OTHER INFORMATION:

(xi) SEQUENCE DESCRIPTION: SEQ ID NO: 163:

Gly Lys Leu Ser Gln Glu Leu His Lys Leu Gln Thr Tyr Pro
                5                         10
Arg Thr Asn Thr
15

(2) INFORMATION FOR SEQ ID NO: 164:

(i) SEQUENCE CHARACTERISTICS:
(A) LENGTH: 17 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 164:

Gly Lys Leu Ser Gln Glu Leu His Lys Leu Gln Thr Tyr Pro
                5                         10
Arg Thr Asn
15

(2) INFORMATION FOR SEQ ID NO: 165:

(i) SEQUENCE CHARACTERISTICS:
(A) LENGTH: 16 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 165:

Gly Lys Leu Ser Gln Glu Leu His Lys Leu Gln Thr Tyr Pro
                5                         10
Arg Thr
15

(2) INFORMATION FOR SEQ ID NO: 166:

(i) SEQUENCE CHARACTERISTICS:
(A) LENGTH: 15 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 166:

Gly Lys Leu Ser Gln Glu Leu His Lys Leu Gln Thr Tyr Pro
                5                         10
Arg
15

(2) INFORMATION FOR SEQ ID NO: 167:

(i) SEQUENCE CHARACTERISTICS:
(A) LENGTH: 21 AMINO ACIDS
(B) TYPE: AMINO ACID
(D) TOPOLOGY: LINEAR (  i i ) MOLECULE TYPE: PEPTIDE (  i x ) FEATURE:
    ( D ) OTHER INFORMATION:

(  x i ) SEQUENCE DESCRIPTION: SEQ ID NO: 167:

Lys Leu Ser Gln Glu Leu His Lys Leu Gln Thr Tyr Pro Arg
                 5                       10
Thr Asn Thr Gly Ser Gly Thr
15                  20

( 2 ) INFORMATION FOR SEQ ID NO: 168:

( i ) SEQUENCE CHARACTERISTICS:
        ( A ) LENGTH: 20 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 168:

Lys Leu Ser Gln Glu Leu His Lys Leu Gln Thr Tyr Pro Arg
                 5                       10
Thr Asn Thr Gly Ser Gly
15                  20

( 2 ) INFORMATION FOR SEQ ID NO: 169:

( i ) SEQUENCE CHARACTERISTICS:
        ( A ) LENGTH: 19 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 169:

Lys Leu Ser Gln Glu Leu His Lys Leu Gln Thr Tyr Pro Arg
                 5                       10
Thr Asn Thr Gly Ser
15

( 2 ) INFORMATION FOR SEQ ID NO: 170:

( i ) SEQUENCE CHARACTERISTICS:
        ( A ) LENGTH: 18 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 170:

Lys Leu Ser Gln Glu Leu His Lys Leu Gln Thr Tyr Pro Arg
                 5                       10
Thr Asn Thr Gly
15

( 2 ) INFORMATION FOR SEQ ID NO: 171:

(i) SEQUENCE CHARACTERISTICS:
(A) LENGTH: 17 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 171:

Lys Leu Ser Gln Glu Leu His Lys Leu Gln Thr Tyr Pro Arg
                 5                       10
Thr Asn Thr
15

(2) INFORMATION FOR SEQ ID NO: 172:

(i) SEQUENCE CHARACTERISTICS:
(A) LENGTH: 16 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 172:

Lys Leu Ser Gln Glu Leu His Lys Leu Gln Thr Tyr Pro Arg
                 5                       10
Thr Asn
15

(2) INFORMATION FOR SEQ ID NO: 173:

(i) SEQUENCE CHARACTERISTICS:
(A) LENGTH: 15 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 173:

Lys Leu Ser Gln Glu Leu His Lys Leu Gln Thr Tyr Pro Arg
                 5                       10
Thr
15

(2) INFORMATION FOR SEQ ID NO: 174:

(i) SEQUENCE CHARACTERISTICS:
(A) LENGTH: 14 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 174:

Lys Leu Ser Gln Glu Leu His Lys Leu Gln Thr Tyr Pro Arg
                 5                       10

(2) INFORMATION FOR SEQ ID NO: 175:

( i ) SEQUENCE CHARACTERISTICS:
    ( A ) LENGTH: 30 AMINO ACIDS
    ( B ) TYPE: AMINO ACID
    ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 175:

Ala Thr Gln Arg Leu Ala Asn Glu Leu Val Lys Ser Ser Asn
                 5                  10

Asn Leu Gly Pro Val Leu Pro Pro Thr Asn Val Gly Ser Asn
15               20                  25

Thr Tyr
    30

( 2 ) INFORMATION FOR SEQ ID NO: 176:

( i ) SEQUENCE CHARACTERISTICS:
        ( A ) LENGTH: 30 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 11 is Orn.

( x i ) SEQUENCE DESCRIPTION: SEQ ID NO: 176:

Ala Thr Gln Arg Leu Ala Asn Asp Leu Val Xaa Ser Ser Asn
                 5                  10

Asn Leu Gly Pro Val Leu Pro Pro Thr Asn Val Gly Ser Asn
15               20                  25

Thr Tyr
    30

( 2 ) INFORMATION FOR SEQ ID NO: 177:

( i ) SEQUENCE CHARACTERISTICS:
        ( A ) LENGTH: 30 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 177:

Ala Thr Gln Arg Leu Ala Asn Glu Leu Val Arg Lys Ser Asn
                 5                  10

Asn Leu Gly Pro Val Leu Pro Pro Thr Asn Val Gly Ser Asn
15               20                  25

Thr Tyr
    30

( 2 ) INFORMATION FOR SEQ ID NO: 178:

( i ) SEQUENCE CHARACTERISTICS:
        ( A ) LENGTH: 30 AMINO ACIDS
        ( B ) TYPE: AMINO ACID
        ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 178:

| Val | Thr | His | Arg | Leu | Ala | Gly | Glu | Leu | Ser | Lys | Ser | Gly | Gly |
|---|---|---|---|---|---|---|---|---|---|---|---|---|---|
| | | | | 5 | | | | | 10 | | | | |

| Val | Val | Lys | Asn | Asn | Phe | Val | Pro | Thr | Asn | Val | Gly | Ser | Lys |
|---|---|---|---|---|---|---|---|---|---|---|---|---|---|
| 15 | | | | | 20 | | | | | 25 | | | |

Ala Phe
    30

( 2 ) INFORMATION FOR SEQ ID NO: 179:

( i ) SEQUENCE CHARACTERISTICS:
        ( A ) LENGTH: 30 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 11 is Orn.

( x i ) SEQUENCE DESCRIPTION: SEQ ID NO: 179:

| Val | Thr | His | Arg | Leu | Ala | Gly | Asp | Leu | Ser | Xaa | Ser | Gly | Gly |
|---|---|---|---|---|---|---|---|---|---|---|---|---|---|
| | | | | 5 | | | | | 10 | | | | |

| Val | Val | Lys | Asn | Asn | Phe | Val | Pro | Thr | Asn | Val | Gly | Ser | Lys |
|---|---|---|---|---|---|---|---|---|---|---|---|---|---|
| 15 | | | | | 20 | | | | | 25 | | | |

Ala Phe
    30

( 2 ) INFORMATION FOR SEQ ID NO: 180:

( i ) SEQUENCE CHARACTERISTICS:
        ( A ) LENGTH: 30 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 180:

| Val | Thr | His | Arg | Leu | Ala | Gly | Glu | Leu | Ser | Arg | Lys | Gly | Gly |
|---|---|---|---|---|---|---|---|---|---|---|---|---|---|
| | | | | 5 | | | | | 10 | | | | |

| Val | Val | Lys | Asn | Asn | Phe | Val | Pro | Thr | Asn | Val | Gly | Ser | Lys |
|---|---|---|---|---|---|---|---|---|---|---|---|---|---|
| 15 | | | | | 20 | | | | | 25 | | | |

Ala Phe
    30

( 2 ) INFORMATION FOR SEQ ID NO: 181:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 11 is Orn.

( x i ) SEQUENCE DESCRIPTION: SEQ ID NO: 181:

Val Leu Gly Lys Leu Ser Gln Asp Leu His Xaa Leu Gln Thr
                 5                      10

Tyr Pro Arg Thr Asn Thr Gly Ser Gly Thr Pro
15                   20                  25

( 2 ) INFORMATION FOR SEQ ID NO: 182:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 182:

Val Leu Gly Lys Leu Ser Gln Glu Leu His Lys Lys Gln Thr
                 5                      10

Tyr Pro Arg Thr Asn Thr Gly Ser Gly Thr Pro
15                   20                  25

( 2 ) INFORMATION FOR SEQ ID NO: 183:

( i ) SEQUENCE CHARACTERISTICS:
        ( A ) LENGTH: 29 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 183:

Thr Gln Arg Leu Ala Asn Glu Leu Val Lys Ser Ser Asn Asn
                 5                      10

Leu Gly Pro Val Leu Pro Pro Thr Asn Val Gly Ser Asn Thr
15                   20                  25

Tyr ( 2 ) INFORMATION FOR SEQ ID NO: 184:

( i ) SEQUENCE CHARACTERISTICS:
        ( A ) LENGTH: 29 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            Xaa at location 10 is Orn.

( x i ) SEQUENCE DESCRIPTION: SEQ ID NO: 184:

Thr Gln Arg Leu Ala Asn Asp Leu Val Xaa Ser Ser Asn Asn
                 5                      10

Leu Gly Pro Val Leu Pro Pro Thr Asn Val Gly Ser Asn Thr
15                   20                  25

Tyr ( 2 ) INFORMATION FOR SEQ ID NO: 185:

( i ) SEQUENCE CHARACTERISTICS:
        ( A ) LENGTH: 29 AMINO ACIDS
        ( B ) TYPE: AMINO ACID (D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 185:

Thr Gln Arg Leu Ala Asn Glu Leu Val Arg Lys Ser Asn Asn
                 5                  10
Leu Gly Pro Val Leu Pro Pro Thr Asn Val Gly Ser Asn Thr
15               20                  25
Tyr (2) INFORMATION FOR SEQ ID NO: 186:

(i) SEQUENCE CHARACTERISTICS:
(A) LENGTH: 29 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 186:

Thr His Arg Leu Ala Gly Glu Leu Ser Lys Ser Gly Gly Val
                 5                  10
Val Lys Asn Asn Phe Val Pro Thr Asn Val Gly Ser Lys Ala
15               20                  25
Phe (2) INFORMATION FOR SEQ ID NO: 187:

(i) SEQUENCE CHARACTERISTICS:
(A) LENGTH: 29 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:
Xaa at location 10 is Orn.

(xi) SEQUENCE DESCRIPTION: SEQ ID NO: 187:

Thr His Arg Leu Ala Gly Asp Leu Ser Xaa Ser Gly Gly Val
                 5                  10
Val Lys Asn Asn Phe Val Pro Thr Asn Val Gly Ser Lys Ala
15               20                  25
Phe (2) INFORMATION FOR SEQ ID NO: 188:

(i) SEQUENCE CHARACTERISTICS:
(A) LENGTH: 29 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 188:

Thr His Arg Leu Ala Gly Glu Leu Ser Arg Lys Gly Gly Val

```
                         5                              10
Val  Lys  Asn  Asn  Phe  Val  Pro  Thr  Asn  Val  Gly  Ser  Lys  Ala
15                       20                       25

Phe
```

(2) INFORMATION FOR SEQ ID NO: 189:

(i) SEQUENCE CHARACTERISTICS:
        (A) LENGTH: 24 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:
            Xaa at location 10 is Orn.

(xi) SEQUENCE DESCRIPTION: SEQ ID NO: 189:

```
Leu  Gly  Lys  Leu  Ser  Gln  Asp  Leu  His  Xaa  Leu  Gln  Thr  Tyr
                    5                        10

Pro  Arg  Thr  Asn  Thr  Gly  Ser  Gly  Thr  Pro
15                       20
```

(2) INFORMATION FOR SEQ ID NO: 190:

(i) SEQUENCE CHARACTERISTICS:
        (A) LENGTH: 24 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 190:

```
Leu  Gly  Lys  Leu  Ser  Gln  Glu  Leu  His  Lys  Lys  Gln  Thr  Tyr
                    5                        10

Pro  Arg  Thr  Asn  Thr  Gly  Ser  Gly  Thr  Pro
15                       20
```

(2) INFORMATION FOR SEQ ID NO: 191:

(i) SEQUENCE CHARACTERISTICS:
        (A) LENGTH: 30 AMINO ACIDS
        (B) TYPE: AMINO ACID
        (D) TOPOLOGY: CIRCULAR BETWEEN
            LOCATIONS 8 AND 25

(ii) MOLECULE TYPE: PEPTIDE (ix) FEATURE:
        (D) OTHER INFORMATION:

(xi) SEQUENCE DESCRIPTION: SEQ ID NO: 191:

```
Val  Thr  His  Arg  Leu  Ala  Gly  Lys  Leu  Ser  Arg  Ser  Gly  Gly
                    5                        10

Val  Val  Lys  Asn  Asn  Phe  Val  Pro  Thr  Asn  Asp  Gly  Ser  Lys
15                       20                       25

Ala  Phe
     30
```

(2) INFORMATION FOR SEQ ID NO: 192:

(i) SEQUENCE CHARACTERISTICS:
        (A) LENGTH: 30 AMINO ACIDS (B) TYPE: AMINO ACID
(D) TOPOLOGY: CIRCULAR BETWEEN
LOCATIONS 9 AND 24

(ii) MOLECULE TYPE: PEPTIDE (ix) FEATURE:
(D) OTHER INFORMATION:

(xi) SEQUENCE DESCRIPTION: SEQ ID NO: 192:

Val Thr His Arg Leu Ala Gly Leu Cys Ser Arg Ser Gly Gly
                5                   10
Val Val Lys Asn Asn Phe Val Pro Thr Cys Val Gly Ser Lys
15                  20                  25
Ala Phe
30

(2) INFORMATION FOR SEQ ID NO: 193:

(i) SEQUENCE CHARACTERISTICS:
(A) LENGTH: 25 AMINO ACIDS
(B) TYPE: AMINO ACID
(D) TOPOLOGY: CIRCULAR BETWEEN
LOCATIONS 9 AND 21

(ii) MOLECULE TYPE: PEPTIDE (ix) FEATURE:
(D) OTHER INFORMATION:

(xi) SEQUENCE DESCRIPTION: SEQ ID NO: 193:

Val Leu Gly Lys Leu Ser Gln Glu Lys His Lys Leu Gln Thr
                5                   10
Tyr Pro Arg Thr Asn Thr Asp Ser Gly Thr Pro
15                  20                  25

(2) INFORMATION FOR SEQ ID NO: 194:

(i) SEQUENCE CHARACTERISTICS:
(A) LENGTH: 25 AMINO ACIDS
(B) TYPE: AMINO ACID
(D) TOPOLOGY: CIRCULAR BETWEEN
LOCATIONS 8 AND 20

(ii) MOLECULE TYPE: PEPTIDE (ix) FEATURE:
(D) OTHER INFORMATION:

(xi) SEQUENCE DESCRIPTION: SEQ ID NO: 194:

Val Leu Gly Lys Leu Ser Gln Cys Leu His Lys Leu Gln Thr
                5                   10
Tyr Pro Arg Thr Asn Cys Gly Ser Gly Thr Pro
15                  20                  25

(2) INFORMATION FOR SEQ ID NO: 195:

(i) SEQUENCE CHARACTERISTICS:
(A) LENGTH: 30 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 195:

Val Thr His Arg Leu Ala Asp Phe Leu Ser Arg Ser Gly Gly

```
                          5                               10
Val  Gly  Lys  Asn  Asn  Phe  Val  Pro  Thr  Asn  Val  Gly  Ser  Lys
15                       20                       25

Ala  Phe
     30
```

( 2 ) INFORMATION FOR SEQ ID NO: 196:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 196:

```
Val  Leu  Gly  Lys  Leu  Ser  Gln  Glu  Leu  His  Lys  Leu  Gln  Thr
                    5                        10

Tyr  Pro  Arg  Thr  Asp  Val  Gly  Ala  Gly  Thr  Pro
15                       20                       25
```

( 2 ) INFORMATION FOR SEQ ID NO: 197:

( i ) SEQUENCE CHARACTERISTICS:
        ( A ) LENGTH: 25 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 197:

```
Val  Leu  Gly  Lys  Leu  Ser  Gln  Glu  Leu  His  Lys  Leu  Gln  Thr
                    5                        10

Tyr  Pro  Arg  Thr  Asn  Thr  Gly  Ser  Asn  Thr  Tyr
15                       20                       25
```

( 2 ) INFORMATION FOR SEQ ID NO: 198:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 198:

```
Leu  Gly  Lys  Leu  Ser  Gln  Glu  Leu  His  Lys  Leu  Gln  Thr  Tyr
                5                       10

Pro  Arg  Thr  Asn  Thr  Gly  Ser  Asn  Thr  Tyr
15                  20
```

( 2 ) INFORMATION FOR SEQ ID NO: 199:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
    ( D ) OTHER INFORMATION:

( x i ) SEQUENCE DESCRIPTION: SEQ ID NO: 199:

Leu Gly Lys Leu Ser Gln Glu Leu His Lys Leu Gln Thr Tyr
                 5                   10
Pro Pro Thr Asn Val Gly Ser Asn Thr Tyr
15                   20

( 2 ) INFORMATION FOR SEQ ID NO: 200:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 200:

Leu Gly Arg Leu Ser Gln Leu Leu His Arg Leu Gln Thr Tyr
                 5                   10
Pro Arg Thr Asn Thr Gly Ser Asn Thr Tyr
15                   20

( 2 ) INFORMATION FOR SEQ ID NO: 201:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 201:

Leu Gly Arg Leu Ser Gln Glu Leu His Arg Leu Gln Thr Tyr
                 5                   10
Pro Arg Thr Asn Thr Gly Ser Asn Thr Tyr
15                   20

( 2 ) INFORMATION FOR SEQ ID NO: 202:

( i ) SEQUENCE CHARACTERISTICS:
        ( A ) LENGTH: 24 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 202:

Leu Gly Lys Leu Ser Gln Glu Leu His Arg Leu Gln Thr Tyr
                 5                   10
Pro Arg Thr Asn Thr Gly Ser Asn Thr Tyr
15                   20

( 2 ) INFORMATION FOR SEQ ID NO: 203:

( i ) SEQUENCE CHARACTERISTICS:
        ( A ) LENGTH: 24 AMINO ACIDS (B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 203:

Leu Gly Arg Leu Ser Gln Glu Leu His Arg Leu Gln Thr Tyr
                  5                  10

Pro Arg Thr Asn Thr Gly Ser Asp Thr Tyr
15                   20

(2) INFORMATION FOR SEQ ID NO: 204:

(i) SEQUENCE CHARACTERISTICS:
(A) LENGTH: 16 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 204:

Val Leu Gly Lys Leu Ser Gln Glu Thr Asn Thr Gly Ser Gly
                  5                  10

Thr Pro
15

(2) INFORMATION FOR SEQ ID NO: 205:

(i) SEQUENCE CHARACTERISTICS:
(A) LENGTH: 11 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 205:

Tyr Pro Arg Thr Asp Val Gly Ala Gly Thr Pro
                  5                  10

(2) INFORMATION FOR SEQ ID NO: 206:

(i) SEQUENCE CHARACTERISTICS:
(A) LENGTH: 25 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 206:

Val Leu Gly Lys Leu Ser Gln Glu Leu His Lys Leu Gln Thr
                  5                  10

Tyr Pro Ser Thr Asn Val Gly Ser Asn Thr Tyr
15                   20                  25

(2) INFORMATION FOR SEQ ID NO: 207:

(i) SEQUENCE CHARACTERISTICS:

(A) LENGTH: 24 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 207:

Leu Gly Lys Leu Ser Gln Glu Leu His Lys Leu Gln Thr Tyr
                  5                           10

Pro Ser Thr Asn Val Gly Ser Asn Thr Tyr
15                  20

(2) INFORMATION FOR SEQ ID NO: 208:

(i) SEQUENCE CHARACTERISTICS:
(A) LENGTH: 30 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 208:

Ala Thr Gln Arg Leu Ala Asn Phe Leu Val His Ser Ser Asn
                  5                           10

Asn Phe Gly Ala Ile Leu Ser Ser Thr Asn Val Gly Ser Asn
15                  20                          25

Thr Tyr
      30

(2) INFORMATION FOR SEQ ID NO: 209:

(i) SEQUENCE CHARACTERISTICS:
(A) LENGTH: 20 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 209:

His Ser Ser Asn Asn Phe Gly Ala Ile Leu Ser Ser Thr Asn
                  5                           10

Val Gly Ser Asn Thr Tyr
15                  20

(2) INFORMATION FOR SEQ ID NO: 210:

(i) SEQUENCE CHARACTERISTICS:
(A) LENGTH: 15 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:

(xi) SEQUENCE DESCRIPTION: SEQ ID NO: 210:

Phe Gly Ala Ile Leu Ser Ser Thr Asn Val Gly Ser Asn Thr
                  5                           10

Tyr
15

( 2 ) INFORMATION FOR SEQ ID NO: 211:

( i ) SEQUENCE CHARACTERISTICS:
        ( A ) LENGTH: 10 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 211:

Ser  Ser  Thr  Asn  Val  Gly  Ser  Asn  Thr  Tyr
               5                            10

( 2 ) INFORMATION FOR SEQ ID NO: 212:

( i ) SEQUENCE CHARACTERISTICS:
        ( A ) LENGTH: 11 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 212:

Tyr  Ser  Ser  Thr  Asn  Val  Gly  Ser  Asn  Thr  Tyr
                     5                           10

( 2 ) INFORMATION FOR SEQ ID NO: 213:

( i ) SEQUENCE CHARACTERISTICS:
        ( A ) LENGTH: 17 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 213:

Ala  Thr  Gln  Arg  Leu  Ala  Asn  Phe  Leu  Val  Arg  Ser  Ser  Asn
                     5                           10

Asn  Leu  Gly
15

( 2 ) INFORMATION FOR SEQ ID NO: 214:

( i ) SEQUENCE CHARACTERISTICS:
        ( A ) LENGTH: 18 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 214:

Arg  Ser  Ser  Asn  Asn  Leu  Gly  Pro  Val  Leu  Pro  Pro  Thr  Asn
                     5                           10

Val  Gly  Ser  Asn
15

( 2 ) INFORMATION FOR SEQ ID NO: 215:

(  i  ) SEQUENCE CHARACTERISTICS:
( A ) LENGTH: 24 AMINO ACIDS
( B ) TYPE: AMINO ACID
( D ) TOPOLOGY: LINEAR (  i i  ) MOLECULE TYPE: PEPTIDE ( i x ) FEATURE:
( D ) OTHER INFORMATION:

( x i ) SEQUENCE DESCRIPTION: SEQ ID NO: 215:

Ala Thr Gln Arg Leu Ala Asn Phe Leu Val Arg Ser Ser Asn
                  5                       10

Asn Leu Thr Asn Val Gly Ser Asn Thr Tyr
15                   20

( 2 ) INFORMATION FOR SEQ ID NO: 216:

(  i  ) SEQUENCE CHARACTERISTICS:
( A ) LENGTH: 11 AMINO ACIDS
( B ) TYPE: AMINO ACID
( D ) TOPOLOGY: LINEAR (  i i  ) MOLECULE TYPE: PEPTIDE ( i x ) FEATURE:
( D ) OTHER INFORMATION:

( x i ) SEQUENCE DESCRIPTION: SEQ ID NO: 216:

Tyr Ser Ser Thr Asn Val Gly Ala Asn Thr Tyr
                  5                       10

( 2 ) INFORMATION FOR SEQ ID NO: 217:

(  i  ) SEQUENCE CHARACTERISTICS:
( A ) LENGTH: 11 AMINO ACIDS
( B ) TYPE: AMINO ACID
( D ) TOPOLOGY: LINEAR (  i i  ) MOLECULE TYPE: PEPTIDE ( i x ) FEATURE:
( D ) OTHER INFORMATION:

( x i ) SEQUENCE DESCRIPTION: SEQ ID NO: 217:

Tyr Val Pro Thr Asn Val Gly Ser Lys Ala Phe
                  5                       10

( 2 ) INFORMATION FOR SEQ ID NO: 218:

(  i  ) SEQUENCE CHARACTERISTICS:
( A ) LENGTH: 30 AMINO ACIDS
( B ) TYPE: AMINO ACID
( D ) TOPOLOGY: LINEAR (  i i  ) MOLECULE TYPE: PEPTIDE ( i x ) FEATURE:
( D ) OTHER INFORMATION:

( x i ) SEQUENCE DESCRIPTION: SEQ ID NO: 218:

Val Thr His Arg Leu Ala Asp Phe Leu Ser Arg Ser Gly Gly
                  5                       10

Val Gly Lys Asn Asn Phe Val Pro Thr Asn Val Gly Ser Lys
15                   20                       25

Ala Phe

30

(2) INFORMATION FOR SEQ ID NO: 219:

(i) SEQUENCE CHARACTERISTICS:
        (A) LENGTH: 11 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 219:

Tyr Pro Arg Thr Asn Thr Gly Ser Asn Thr Tyr
              5                        10

(2) INFORMATION FOR SEQ ID NO: 220:

(i) SEQUENCE CHARACTERISTICS:
        (A) LENGTH: 11 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 220:

Tyr Pro Arg Thr Asn Thr Gly Ser Arg Thr Tyr
              5                        10

(2) INFORMATION FOR SEQ ID NO: 221:

(i) SEQUENCE CHARACTERISTICS:
        (A) LENGTH: 11 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 221:

Tyr Pro Arg Thr Asn Thr Gly Ser Lys Thr Tyr
              5                        10

(2) INFORMATION FOR SEQ ID NO: 222:

(i) SEQUENCE CHARACTERISTICS:
        (A) LENGTH: 11 AMINO ACIDS
        (B) TYPE: AMINO ACID
        (D) TOPOLOGY: LINEAR (ii) MOLECULE TYPE: PEPTIDE (ix) FEATURE:
        (D) OTHER INFORMATION:

(xi) SEQUENCE DESCRIPTION: SEQ ID NO: 222:

Tyr Pro Arg Thr Asn Val Gly Ser Asn Thr Tyr
              5                        10

(2) INFORMATION FOR SEQ ID NO: 223:

(i) SEQUENCE CHARACTERISTICS:
        (A) LENGTH: 11 AMINO ACIDS
        (B) TYPE: AMINO ACID (D) TOPOLOGY: LINEAR (i i) MOLECULE TYPE: PEPTIDE (i x) FEATURE:
    (D) OTHER INFORMATION:

(x i) SEQUENCE DESCRIPTION: SEQ ID NO: 223:

Tyr Pro Arg Thr Asn Val Gly Ala Asn Thr Tyr
                  5                   10

(2) INFORMATION FOR SEQ ID NO: 224:

(i) SEQUENCE CHARACTERISTICS:
        (A) LENGTH: 11 AMINO ACIDS
        (B) TYPE: AMINO ACID
        (D) TOPOLOGY: LINEAR (i i) MOLECULE TYPE: PEPTIDE (i x) FEATURE:
        (D) OTHER INFORMATION:

(x i) SEQUENCE DESCRIPTION: SEQ ID NO: 224:

Tyr Pro Arg Thr Asn Thr Gly Ala Asn Thr Tyr
                  5                   10

(2) INFORMATION FOR SEQ ID NO: 225:

(i) SEQUENCE CHARACTERISTICS:
        (A) LENGTH: 30 AMINO ACIDS
        (B) TYPE: AMINO ACID
        (D) TOPOLOGY: CIRCULAR BETWEEN
            LOCATIONS 5 AND 8

(i i) MOLECULE TYPE: PEPTIDE (i x) FEATURE:
        (D) OTHER INFORMATION:

(x i) SEQUENCE DESCRIPTION: SEQ ID NO: 225:

Val Thr His Arg Cys Ala Gly Cys Leu Ser Arg Ser Gly Gly
                5                   10
Val Val Lys Asn Asn Phe Val Pro Thr Asn Val Gly Ser Lys
15              20                  25
Ala Phe
30

(2) INFORMATION FOR SEQ ID NO: 226:

(i) SEQUENCE CHARACTERISTICS:
        (A) LENGTH: 19 AMINO ACIDS
        (B) TYPE: AMINO ACID
        (D) TOPOLOGY: LINEAR (i i) MOLECULE TYPE: PEPTIDE (i x) FEATURE:
        (D) OTHER INFORMATION:

(x i) SEQUENCE DESCRIPTION: SEQ ID NO: 226:

Ala Thr Gln Arg Leu Ala Asn Phe Leu Val Arg Thr Asn Val
                5                   10
Gly Ser Asn Thr Tyr
15

(2) INFORMATION FOR SEQ ID NO: 227:

(i) SEQUENCE CHARACTERISTICS:

(A) LENGTH: 25 AMINO ACIDS
(B) TYPE: AMINO ACID
(D) TOPOLOGY: LINEAR (ii) MOLECULE TYPE: PEPTIDE (ix) FEATURE:
(D) OTHER INFORMATION:
Xaa at location 1 is Val, Ala or no amino
acid residue; Xaa at location 4 is Lys, Arg
or Orn; Xaa at location 8 is Glu, Asp, Leu
or Phe; Xaa at location 11 is Lys, Arg or
Orn; Xaa at location 20 is Thr or Val; Xaa
at location 22 is Ser or Ala; Xaa at
location 23 is Gly, Asn, Lys, Arg or Orn;
and Xaa at location 25 is Pro, Tyr or Phe.

(xi) SEQUENCE DESCRIPTION: SEQ ID NO: 227:

Xaa Leu Gly Xaa Leu Ser Gln Xaa Leu His Xaa Leu Gln Thr
              5                   10

Tyr Pro Arg Thr Asn Xaa Gly Xaa Xaa Thr Xaa
15              20              25